United States Patent
Ornatsky

(10) Patent No.: US 10,577,648 B2
(45) Date of Patent: Mar. 3, 2020

(54) METHODS OF USING INDUCTIVELY COUPLED PLASMA MASS SPECTROSCOPY SYSTEMS FOR ANALYZING A CELLULAR SAMPLE

(71) Applicant: Fluidigm Canada Inc., Markham (CA)

(72) Inventor: Olga Ornatsky, Richmond Hill (CA)

(73) Assignee: FLUIDIGM CANADA INC., Markham (CA)

( * ) Notice: Subject to any disclaimer, the term of this patent is extended or adjusted under 35 U.S.C. 154(b) by 613 days.

(21) Appl. No.: 14/823,980

(22) Filed: Aug. 11, 2015

(65) Prior Publication Data

US 2016/0097089 A1 Apr. 7, 2016

Related U.S. Application Data

(63) Continuation of application No. 11/674,513, filed on Feb. 13, 2007, now abandoned.

(60) Provisional application No. 60/772,588, filed on Feb. 13, 2006.

(51) Int. Cl.
| | | |
|---|---|---|
| G01N 33/00 | (2006.01) |
| C12Q 1/6825 | (2018.01) |
| C12Q 1/6816 | (2018.01) |
| C12Q 1/6841 | (2018.01) |
| G01N 33/543 | (2006.01) |
| G01N 33/58 | (2006.01) |
| G01N 33/68 | (2006.01) |
| H01J 49/00 | (2006.01) |

(52) U.S. Cl.
CPC ......... *C12Q 1/6825* (2013.01); *C12Q 1/6816* (2013.01); *C12Q 1/6841* (2013.01); *G01N 33/543* (2013.01); *G01N 33/58* (2013.01); *G01N 33/6848* (2013.01); *H01J 49/0027* (2013.01); *G01N 2458/15* (2013.01); *G01N 2560/00* (2013.01)

(58) Field of Classification Search
None
See application file for complete search history.

(56) References Cited

U.S. PATENT DOCUMENTS

| | | |
|---|---|---|
| 4,022,876 A | 5/1977 | Anbar |
| 4,205,952 A | 6/1980 | Cais |
| 4,683,195 A | 7/1987 | Mullis et al. |
| 4,683,202 A | 7/1987 | Mullis et al. |
| 4,800,159 A | 1/1989 | Mullis et al. |
| 5,079,172 A | 1/1992 | Hari et al. |
| 5,521,289 A | 5/1996 | Hainfeld et al. |
| 5,559,337 A | 9/1996 | Ito et al. |
| 5,569,754 A | 10/1996 | Williams et al. |
| 5,773,823 A | 6/1998 | Ito et al. |
| 5,804,821 A | 9/1998 | Nakagawa |
| 5,981,180 A | 11/1999 | Chandler et al. |
| 6,031,379 A | 2/2000 | Takada et al. |
| 6,116,516 A | 9/2000 | Ganan-Calvo |
| 6,119,953 A | 9/2000 | Ganan-Calvo et al. |
| 6,225,636 B1 | 5/2001 | Ginestet |
| 6,344,316 B1 | 2/2002 | Lockhart et al. |
| 6,444,650 B1 * | 9/2002 | Cech .............. C12Y 207/07049 514/44 A |
| 6,444,661 B1 * | 9/2002 | Barton .................. C07F 15/008 514/185 |
| 6,449,562 B1 | 9/2002 | Chandler et al. |
| 6,524,793 B1 | 2/2003 | Chandler et al. |
| 6,630,296 B2 | 10/2003 | Xue et al. |
| 6,836,742 B2 | 12/2004 | Brekenfeld |
| 6,858,711 B2 | 2/2005 | MeGa, II et al. |
| 7,135,296 B2 | 11/2006 | Baranov et al. |
| 2003/0064364 A1 | 4/2003 | Lockhart et al. |
| 2003/0092090 A1 * | 5/2003 | Hajizadeh ............ G01N 33/543 435/7.92 |
| 2004/0059519 A1 | 3/2004 | Chandler et al. |
| 2004/0072250 A1 * | 4/2004 | Baranov ................ G01N 33/58 435/7.1 |
| 2004/0077100 A1 * | 4/2004 | Sekar ................... C12Q 1/6837 436/172 |

(Continued)

FOREIGN PATENT DOCUMENTS

| | | |
|---|---|---|
| JP | 2005-532058 | 10/2005 |
| WO | 9504160 A1 | 2/1995 |

(Continued)

OTHER PUBLICATIONS

"How many species of bacteria are there?" (WiseGeek.com, accessed Jan. 21, 2014).*
"List of sequenced bacterial genomes" (Wikipedia.com; accessed Jan. 24, 2014).*
Baranov et al. "A sensitive and quantiative element-tagged immunoassay with ICPMS detection," Anal Chm, 2002, vol. 74, pp. 1629-1636.
Baronov et al., "The potential for elemental analysis in biotechnology", J. Anal. At. Spectrom., 2002, 17, 1148-1152.
Betimer et al., "Elemental tagging in inorganic mass spectrometric bioanalysis", Anal Bioanal Chem 2006, 386, 7-11.
Cao et al. "DNA-modified core-shell Ag/Au nanoparticles," J Am Chem Soc, 2001, vol. 123, No. 32, pp. 7961-7962.
Chen et al., "Nuclear Localizing Sequences Promote Nuclear and Enhance the Radiotoxicity of the Anti-CD33 Monoclonal . . . " The Journal of Nuclear Medicine 2006, 47, 5, 827-836.

(Continued)

*Primary Examiner* — Bradley L. Sisson
(74) *Attorney, Agent, or Firm* — Kilpatrick Townsend & Stockton LLP

(57) ABSTRACT

The invention relates to the use of inductively coupled plasma mass spectroscopy for cellular sample analysis. In some embodiments a method of performing mass spectroscopy analysis using an inductively coupled plasma mass spectroscopy system is provided. The method may include introducing a cellular sample comprising one or more cells or cellular particles into an inductively coupled plasma of the inductively coupled plasma mass spectroscopy system. The method may further include using the inductively coupled plasma mass spectroscopy system to assess the cellular sample by detecting and measuring one or more element tags in the cellular sample based on the element or isotopic compositions of the one or more element tags.

22 Claims, 7 Drawing Sheets

Specification includes a Sequence Listing.

(56) References Cited

U.S. PATENT DOCUMENTS

| | | |
|---|---|---|
| 2004/0126901 A1 | 7/2004 | Kauvar et al. |
| 2004/0143109 A1 | 7/2004 | Trebesius et al. |
| 2005/0158772 A1 | 7/2005 | Lockhart et al. |
| 2005/0191646 A1 | 9/2005 | Lockhart et al. |
| 2005/0218319 A1 | 10/2005 | Bandura et al. |
| 2006/0003366 A1 | 1/2006 | DiCesare |
| 2006/0040315 A1 | 2/2006 | Rothstein et al. |
| 2006/0046254 A1 | 3/2006 | Xie et al. |
| 2006/0177850 A1 | 8/2006 | Schermer et al. |
| 2006/0240411 A1 | 10/2006 | Mehrpouyan et al. |
| 2006/0240444 A1 | 10/2006 | Chu |
| 2006/0246530 A1 | 11/2006 | Krause et al. |
| 2007/0037215 A1 | 2/2007 | Patton |
| 2007/0105990 A1 | 5/2007 | Makino et al. |
| 2007/0190560 A1 | 8/2007 | Bradley et al. |
| 2008/0176334 A1 | 7/2008 | Baranov et al. |

FOREIGN PATENT DOCUMENTS

| | | |
|---|---|---|
| WO | 95/21944 A | 8/1995 |
| WO | 2004/005545 | 1/2004 |
| WO | 2004/005545 A1 | 1/2004 |
| WO | 2005/001143 | 1/2005 |
| WO | 2005/003767 A2 | 1/2005 |
| WO | 2005/123959 A2 | 12/2005 |
| WO | 2006/007567 | 1/2006 |
| WO | 2006/109073 A | 10/2006 |
| WO | 2007/137418 A | 6/2007 |
| WO | 2007/082833 A1 | 7/2007 |
| WO | 2007/093049 A | 8/2007 |
| WO | 2007/093050 A | 8/2007 |
| WO | 2007/140571 A1 | 12/2007 |
| WO | 2008/080224 A | 10/2008 |

OTHER PUBLICATIONS

Churchill et al., "Fundamentals of experimental design for eDNA microarrays", Nature Genetics Supplement 2002, 32, 490-495.

Derradji et al., "Comparison of Different Protocols for Telomore Length Estimation by Combination of Quantative Fluorescen . . . ", Anticancer Research 25:1039-1050 (2005).

European Search Report and Opinion dated Mar. 23, 2010 with respect to corresponding European Patent Application No. 07 71 0634.

Graviti et al., Genotyping of 27 Human Papillomavirus Types by Using L 1 Consensus PCR Products by a Single- . . . Journal of Clinical Microbiology 1998, 36, 10, 3020-3027.

Guo et al., "Direct fluorescence analysis of genetic polymorphisms by hybridization with oligonucleotide arrays on glass . . . ", Nucleic Acids Research 1994, 22, 24, 5456-5465.

Hu et al., "Detection of Multiple Proteins on One Spot by Laser Ablation Inductively Coupled Plasma Mass 6 Spectrometry and Application to . . . " Anal. Chem. 2007, 79, 923-929.

International Search Report and Written Opinion dated Aug. 28, 2008 for PCT Patent Application No. PCT/CA2007/000223, 11 pages.

Jakubowski et al., "Labelling of proteins by sue of iodination and detection by ICP-MS", J. Anal. At. 1 Spectrom., 2008, 23, 1487-1496.

Jakubowski et al., "Labelling of proteins with 2-(4-isothiocyanatobenzyl)-1,4,7,10• tetraacetic . . . "-ICP-ms, J. Anal. At. Spectrum., 2008, 23, 1497-1507.

Jakubowski et al., "Metallobiomolecules. The basis of life, the challenge of atomic spectroscopy", J. Anal. At. Spectrum, 2004, 19, 1-4.

Janicki et al., "From Silencing to Gene Expression Real-Time Analysis in Single cells", Cell vol. 116, 683-698, Mar. 15, 2007.

Jonker et al., "Towards Quantitative In Situ Hybridization", The Journal of Histochemistry & Cytochemistry 1997,45,3,413-423.

Kadkol et al., In Situ Hybridization Theory and Practice•, Molecular Diagnosis 1999,4, 3, 169-183.

Levsky et al., Fluorescence in situ hybridization: past, present and future•, Journal of Cell Science 2003, 116, 14, 2833-2838.

Levsky et al., Single-Cell Gene Expression Profiling, Science 2002, 297, 836-840.

Lipshutz et al., "High density synthetic oligonucleotide arrays", Nature Genetics Supplement 1999, 21, 20-24.

Lou et al., "Polymer-Based Elemental Tags for Sensitive Bioassays", Angew. Chem. Int. Ed. 2007, 46, 6111-6114.

Merkoci et al., Toward an ICPMS-Linked DNA Assay Based on Gold Nanoparticles Immunoconnected through 2 Peptide Sequences•, Anal. Chern. 2005, 77, 6500-6503.

Ornatsky et al, "Multiple cellular antigen detection by ICP-MS", Journal of Immunological Methods 2006, 308,68-76.

Ornatsky et al., "Development of analytical methods for multiplex bio-assay with inductively coupled plasma mass spectrometry", J. Anal. At. Spectrom., 2008, 23, 463-469.

Ornatsky et al., "Study of Cell Antigens and Intracellular DNA by Identification of Element-Containing Labels and . . . ",Anal. Chem. 2008, 2539-2547.

Ornatsky, O. et al. "Messenger RNA detection in leukemia cell lines by novel metal-tagged in situ hybrdization using inductively coupled plasma mass spectrometry," Translational Oncogenomics, Sep. 2006, vol. 1, pp. 1-9.

Pease et al., 'Light-generated oligonucleotide arrays for rapid DNA sequence analysis', Biochemistry 1994, 91, 5022-5026.

Quinn et al. "Simultaneous determination of proteins using an element-tagged immunoassay coupled with ICP-MS detection," J. Anal At Spectrom, 2002, vol. 17, 892-896.

Raap et al., 'Advances in fluorescence in situ hybridization', Mutation Research 400, 1998, 287-298.

Razumienko et al, "Element-tagged immunoassay with ICP-MS detection: Evaluation and comparison to conventional immunoassays", Journal of Immunological Methods 2008, 336, 56-63.

Scheffer et al., "ICP-MS as a new tool for the determination of gold nanoparticles in bioanalytical 3 applications", Anal Bioanal Chem (2008) 390, 249-252.

Stein et al. "Physiochemical Properties of Phosphorothioate Oligodeoxynucleotides," Nuc Acid Res, 1988, No. 16. No. 8, pp. 3209-3321.

Tanke et la. "FISH and immunocytochemistry: towards visualising single target molecules in living cells," Current Opinion in Biotechnology, 2005, vol. 16, pp. 49-54.

Tanner et al., "Flow cytometer with mass spectrometer detection for massively multiplexed single-cell biomarker assay", PureAppl. Cham. 2008,80, 12,2627-2641.

Tanner et al., "Multiplex bio-assay with inductively coupled plasma mass spectrometry: Towards a massively multivariate" . . . "Spectrochimica Acta" Part B 62 (2007) 188-195.

Thomas, R.N. et al. "Nanopshere-Antibody Conjugates with Releasable Fluorescent Probes," 2001, Fresenius J Anal Chem, vol. 369, pp. 477-482.

Unwin et al., "Relative quantification in proteomics: new approaches for biochemistry", TRENDS in 4 Biochemical Sciences 2006, 31, 8, 473-484.

Vancaeyzeele et al., "Lanthanide-Containing Polymer Nanoparticles for Biological Tagging Applications: Nonspecific Endocytosis . . . ", J. Am. Chem. Soc. 2007, 129, 13653-13660.

Venkatasubbarao et al. "Microarrays—Status and Prospects," TRENDS in Biotechnology, Dec. 2004, vol. 22, No. 12, pp. 630-637.

Weeratna et al. "Gene Expression Profiling: From Microarrays to Medicine," J Clin Immunol, May 2004, vol. 24, No. 3, pp. 213-224.

Weier et al. "Applications and technical challenges of fluorescence in situ hybridization in stem cell research," Blood Cells, Molecules and Diseases, 2004, vol. 32, pp. 68-76.

Wikipedia, "Fungi," located at www.wikipedia.com, last visited on Jun. 3, 2013, 28 pages.

Wikipedia, "List of Sequenced Baterial Genomes," located at www.wikipedia.com, last visited on Jan. 24, 2014, 57 pages.

Wikipedia, "Mammal," located at www.wikipedia.com, last visited on Sep. 22, 2011, 17 pages.

Wikipedia, "Murinae," located at www.wikipedia.com, last visited on Mar. 18, 2013, 21 pages.

(56) References Cited

OTHER PUBLICATIONS

Wikipedia, "Plant," located at www.wikipedia.com, last visited on Mar. 8, 2013, 12 pages.
Wikipedia, "Viruses," located at www.wikipedia.com, last visited on Nov. 24, 2012, 34 pages.
WiseGEEK.com, "How Many Species of Bateria Are There?" located at http://www.wisegeek.com/how-many-species-of-bacteria-are-tehre.htm, last vistied on Sep. 23, 2011, 6 pages.
Xu et al., Preparation and Preliminary Evaluation of a Biotin-Targeted, Lectin-Targeted Dendrimer-Based Probe for Dual-Modality Magnetic . . . Chem. 2007, 18, 1474-1482.
Zhang et al., "A novel combination of immunoreaction and ICP-MS as a hyphenated technique for the 8 determination ofthyroid-stimul. . . ", J. Anal. At. Spectrom., 2002, 17, 1396.
Zhang et al., "Application of the Biological Conjugate between Antibody and Colloid Au Nanoparticles as Analyte to 5 Inductively Coupled Plasma . . . ", Anal. Chem. 2002, 74, 96-99.
Zhang et al., "ICP-MS-based competitive immunoassay for the determination of total thyroxin in human serum", J. 9 Anal. At. Spectrom., 2002, 17, 1304-1307.
Zhang et al.: "Simultaneous Determination of a-Fetoprotein and Free 13-Human Chorionic Gonadotropin by 7 Element-Tagged Immunoassay . . . " Clinical Chemistry 2004, 50 7, 1214-1221.
Zhang et al. "Rapid detection of leukemia-associated translocation fusion genese using a novel combined RT-PCR and flow cytometric method," Leukemia, 2002, vol. 16, pp. 144-149.
Isola, N.R. et al., "MALDI-TOF Mass Spectrometric Method for Detection of Hybridized DNA Oligomers," Anal. Chem., 2001, vol. 73, pp. 2126-2131.
Arlinghaus et al., "Multiplexed DNA Sequencing and Diagnostics by Hybridization With Enriched Stable Isotope Labels", Analytical Chemistry, American Chemical Society, US, vol. 69, No. 8, Apr. 15, 1997, pp. 1510-1517.
Samiotaki et al., "Seven-Color Time-Resolved Fluorescence Hybridization Analysis of Human Papilloma Virus Types", Analytical Biochemistry, Elsevier, Amsterdam, NL, vol. 253, No. 2, Nov. 15, 1997, pp. 156-161.

\* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: oligo probe

<400> SEQUENCE: 1
atccaacgct tggtgaattc                                              20
```

METHODS OF USING INDUCTIVELY COUPLED PLASMA MASS SPECTROSCOPY SYSTEMS FOR ANALYZING A CELLULAR SAMPLE

SEQUENCE LISTING

The sequence listing submitted via EFS-web, in compliance with 37 CFR 1.52(e)(5), is incorporated herein by reference. The sequence listing text file contains the file "Sequence Listing," created on Aug. 11, 2015, which is 410 bytes in size.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD

The invention relates to the use of inductively coupled plasma mass spectroscopy for cellular sample analysis.

INTRODUCTION

Biological "samples" refers to any sample of a biological nature that requires analysis. For example, samples may include biological molecules, tissue, fluid, and cells of an animal, plant, fungus, or bacteria. They may also include molecules of viral origin. Typical samples include, but are not limited to, sputum, blood, blood cells (e.g., white cells), tissue or fine needle biopsy samples, urine, peritoneal fluid, and pleural fluid, or cells there from. Biological samples may also include sections of tissues such as frozen sections taken for histological purposes. Another typical source of biological samples are viruses and cell cultures of animal, plant, bacteria, fungi where gene expression states can be manipulated to explore the relationship among genes. Other examples are known to those skilled in the art.

"RNA sample" is an ribonucleic acid (RNA) preparation of a biological sample. It includes not only the mature mRNA, but also the RNA processing intermediates and nascent pre-mRNA transcripts. For example, total mRNA purified with poly (T) column contains RNA molecules with poly (A) tails. Those poly A+RNA molecules could be mature mRNA, RNA processing intermediates, nascent transcripts or degradation intermediates.

"Nucleic acid" as used herein refers to a deoxyribonucleotide or ribonucleotide polymer in either single or double-stranded form such as any DNA or RNA or DNA/RNA hybrid molecule. The term refers to any DNA including, but not limited to, genomic DNA, mitochondrial DNA, plasmid DNA, chloroplast DNA, cDNA, amplified DNA or RNA fragments, total RNA, messenger RNA, small nuclear RNA.

"Oligonucleotide" is a single-stranded nucleic acid ranging in length from 2 to about 1000 nucleotides, more typically from 2 to about 500 nucleotides in length. It may also include "locked nucleic acid" molecules (LNA).

"LNA" refers to bi-cyclic high-affinity RNA analogs in which the furanose ring of the ribose sugar is chemically locked in an RNA-mimicking conformation by the introduction of an $O2',C4'$-methylene bridge, resulting in unprecedented hybridization affinity toward complementary DNA and RNA molecules. The thermal stability and improved mismatch discrimination of short LNA-modified oligonucleotides has made them useful for single nucleotide polymorphism (SNP) genotyping assays, antisense-based gene silencing and gene expression profiling.

"Target nucleic acid" refers to a nucleic acid (often derived from a biological sample and hence referred to also as a sample nucleic acid), to which a complementary oligonucleotide probe specifically hybridizes. The target nucleic acids can be derived from any source of nucleic acids (e.g., including, but not limited to chemical syntheses, amplification reactions, forensic samples, etc.). It is either the presence or absence of one or more target nucleic acids that are to be detected, or the amount of one or more target nucleic acids that is to be quantified. The target nucleic acid(s) that are detected preferentially have nucleotide sequences that are complementary to the nucleic acid sequences of the corresponding oligonucleotide probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. Other variations of this definition are known to those skilled in the art.

"Probe" refers to a nucleic acid that binds to a target nucleic acid of complementary sequence through complementary base pairing, usually hydrogen bond formation. As used herein, an oligonucleotide probe may include natural (i.e. A, G, C, or T) or modified bases (for example, but not limited to, 7-deazaguanosine, inosine, etc.) as is known to those skilled in the art. In addition, the bases in an oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages. Expression of a particular transcript may be detected by a plurality of probes, typically, 5, 10, 15, 20, 30 or 40 probes. Each of the probes may target different sub-regions of the transcript. However, probes may overlap over targeted regions. Probes may be selected or designed using a selection program such as Primer3 from Massachusetts Institute of Technology (MIT). According to the invention, probes may be labeled with an elemental tag at the 3' or 5' end, or in the middle of the oligonucleotide. In one embodiment, the probes are immobilized to the support through the one of the ends. Other examples of probe are known to those skilled in the art.

"A support" is a surface which has been functionalized by, for example, pyrrole-2,5-dione (maleimido), sulfonic acid anion, or p-(chloromethyl) styrene but not limited to these. A support may, for example, be a synthetic membrane, bead (polystyrene, agarose, silica, etc.), planar surface in plastic microwells, glass slides, reaction tubes, etc. (not limited to these). The function of a support is to act as a solid phase for the coupling of probes or target molecules. Yet in another variation of this definition, which is known to those skilled in the art, the support means any surface between two different states of matter: liquid and solid, solid and solid, liquid and liquid, liquid and gas, gas and solid and so on.

"Coupled to a support" means bound directly or indirectly thereto including attachment by covalent binding, hydrogen bonding, ionic interaction, hydrophobic interaction, or using specific ligands attached to the end of the oligonucleotide probe for specific interaction with ligand-binding molecules attached to the support, for example a bead. For example, such a system may include biotin-streptavidin, where the probe carries a biotin moiety and the support is coated with streptavidin. Covalent chemical attachment of the oligonucleotide probe to the support can be accomplished through the 5'-phosphate on the nucleic acid to the coated support through a phosphamidate bond. Coupled to support may be achieved by means of a spacer molecule to provide a space between the double stranded part of the probe and target. Such methods for the immobilization of oligonucleotides to supports are well established in the art[2-4]. Yet in another variation of this definition, which is known to those skilled in the art, the coupling to support means functional attachment to boundary between two different states of matter: liquid and solid, solid and solid, liquid and liquid, liquid and gas, gas and solid and so on.

"Element labeled bead" is a type of support bead (for example, but not limited to, polystyrene, agarose, silica, etc.) which functionally incorporates or is imbibed with an element or multitude of elements with one or many isotopes. As is known to those skilled in the relevant arts, an element can be an atomic part of chemical moiety.

"Uniquely labeled bead" refers to a physical entity of a multitude of atoms of one or more isotopes of one or more elements imbibed in a bead such that one type of said bead labeled with one type of said elements is distinguishable from any other type of said elements by elemental analysis. Each uniquely labeled support bears a multitude of similar or different oligonucleotides capable of hybridizing specifically to a particular target nucleic acid.

"Element tag" is a chemical moiety which includes an elemental atom or multitude of elemental atoms with one or many isotopes attached to a supporting molecular structure. The element tag also comprises the means of attaching the tag to a substrate, which can include (but is not limited to) pyrrole-2,5-dione (maleimido), sulfonic acid anion, or p-(chloromethyl)styrene (for thiol, N-terminus, or C-terminus, respectively). An elemental tag may be distinguishable from a multitude of other element tags in the same sample because its elemental or isotopic composition is different than that of the other tags.

"Transition element" means any element having the following atomic numbers, 2-29, 39-47, 57-79 and 89. Transition elements include the rare earth elements, lanthanides and noble metals. (Cotton and Wilkinson, 1972).

An "affinity product" or "affinity reagent" refers to biological molecules (antibody, aptamer, lectin, sequence-specific binding peptide, etc.) which are known to form highly specific non-covalent bonds with respective target molecules (peptides, antigens, small molecules, etc.). Affinity reagent labeled with a unique element tag is an affinity product labeled with an element tag that is unique and distinguishable from a multitude of other element tags in the same sample.

"Hybridizes specifically to", refers to the binding, duplexing, or hybridizing of a nucleic acid molecule preferentially to a particular nucleotide sequence under stringent conditions when that sequence is present in a complex mixture (e.g., total cellular) DNA or RNA. Optimization of hybridization conditions is well known to those of skill in the art and are reviewed in WO 95/219445. The term "stringent conditions" refers to conditions under which a probe will hybridize preferentially to its target subsequence, and to a lesser extent to, or not at all to, other sequences. Stringent conditions are sequence-dependent and will be different in different circumstances. Longer sequences hybridize specifically at higher temperatures. Typically, stringent conditions will be those in which the salt concentration is at least about 0.01 to 1.0 M Na+ (or other salts) at pH 7.0 to 8.3 and the temperature is at least about 30° C. for short probes (e.g., 10 to 50 nucleotides). Stringent conditions may also be achieved with the addition of destabilizing agents such as formamide, as is known to those skilled in the art.

"In situ hybridization" refers to a hybridization technique in which the hybridization reaction between the complementary single-stranded nucleic acid probe and endogenous target is carried out in specially prepared cells or histological sections without purification of target nucleic acid.

"Background signal intensity" refers to hybridization signals resulting from non-specific binding, or other interactions, between the target nucleic acids and labeled oligonucleotide (e.g., the oligonucleotide probes, control probes, etc.).

"Mismatch probes" provide a control for non-specific binding or cross-hybridization to a nucleic acid in the sample other than the target to which the probe is directed.

"Oligo(dT)n-elemental tag" is a metal labeled oligonucleotide comprised of a number (n) of deoxythimidine triphosphate nucleosides and additional nucleosides as in oligo (dT)-LNA complex, used as hybridization probe for polyadenylation regions of mRNA. The number of deoxythimidine triphosphate nucleosides can range from about 6 to about 50.

"Elemental analysis" is a process where a sample is analyzed for its elemental composition and sometimes isotopic composition. Elemental analysis can be accomplished by a number of methods, including: optical atomic spectroscopy, such as flame atomic absorption, graphite furnace atomic absorption, and inductively coupled plasma atomic emission, which probe the outer electronic structure of atoms; mass spectrometric atomic spectroscopy, such as inductively coupled mass spectrometry, which probes the mass of atoms; X-ray fluorescence, particle induced x-ray emission, x-ray photoelectron spectroscopy, and Auger electron spectroscopy which probes the inner electronic structure of atoms.

"Elemental analyzer" is an instrument for the quantitation of the atomic composition of a sample employing one of the methods of elemental analysis.

"Particle elemental" analysis is a process where an analyzed sample, composed of particles dispersed in a liquid (beads in buffer, for example), is interrogated in such manner that the atomic composition is recorded for individual particles (bead-by-bead, for example). An example of the analytical instrument is a mass spectrometer-based flow cytometer.

"Solution elemental analysis" is a process where an analyzed sample is interrogated in such manner that the atomic composition is averaged over the entire volume of the sample.

"An internal standard" is defined as a known amount of a compound, different from analyte that is added to the unknown. Signal from analyte is compared with signal from the internal standard to find out how much analyte is present. An internal standard may be used when performing mass spectrometry quantitation. An internal standard can be also used by other means known to those skilled in the art.

"Fixing and permeabilization" refers to chemical cross-linking of cellular components by agents such as glutaraldehyde, formaldehyde, formalin, ethanol, methanol, etc., and creating holes in the cell membrane with detergents. Suitable detergents may be readily selected from among non-ionic detergents. Desirably, these detergents are used at a concentration between about 0.001% to about 0.1%. One detergent that may be used is Triton X-100 (Sigma T9284). Examples of other suitable detergents include Igepal and Nonidet P-40. Other suitable detergent may be readily selected by one of skill in the art.

The Human Genome project has opened access to a wealth of genetic sequence information that will help diagnose and treat many types of human diseases. However, gene profiling in medicine requires fine-tuning of existing methods and introduction of new sensitive and robust technologies. Genomic screening methods for monitoring thousands of genes simultaneously include such technologies as DNA microarrays, differential display, and serial analysis of gene expression (SAGE). The basic principle of all arrays is the hybridization of fluorescent or biotin labeled cRNA or cDNA species generated from sample RNA to oligonucleotides or complementary DNA molecules attached to solid supports. Presently, gene chip arrays are the predominant platform used, where a slide glass surface is the substrate and fluorescence-method of detection[6-10]. Alternative to planar microarrays are bead arrays being developed by Luminex, BD Biosciences, Illumina and many others. Microsphere arrays are created by either impregnating beads with different ratios of fluorescent dye or combinations of quantum dots or by physically etching barcodes on the bead surface[11]. Microarrays essentially represent cumulative signals from many individual cells and involve loss of information concerning single cells. Sample preparation and universal reference standards are critical since genomic information obtained from a heterogeneous population of cells will interfere with the gene profile of a particular cancer cell.

DNA diagnostic methods usually involve amplification of target sequences to increase the sensitivity and specificity of the assays through polymerase chain reaction (PCR) or other similar amplification technologies. In the PCR method[12] two primer sequences are prepared which are complementary to regions on opposite complementary strands of the target sequence. An excess of deoxynucleoside triphosphates are added to a reaction mixture along with a thermostable DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers reaction products will dissociate from the target to become new targets. The excess primers will bind to the target and to the reaction products and the process is repeated.

Several methods for multiplexed detection of nucleic acids in single cells exist, but they do not currently combine quantification with massive multiplexing. Semi-quantitative in situ hybridization histochemistry (ISH) is a technique used to detect the presence and estimate the relative abundance of specific RNA sequences in a single cell[13;14]. The visualization of signal is usually achieved by chromogenic substrates or fluorochrome dyes and is not readily amenable to multiplexing. Cytogeneticists have also developed a unique chromosome characterization method termed fluorescent in situ hybridization (FISH)[15-17], which uses fluorescently labeled nucleic acids to visualize complementary sequences by hybridization in both fixed biological structures and living cells. RNA FISH aims to localize mRNA to its transcription site in a cellular compartment. Work by Levsky and co-workers[18] employing advanced computational fluorescence microscopy and multiplex oligomer DNA probes has demonstrated the feasibility of generating a simultaneous FISH profile for eleven genes in the nuclei of in vitro cultured cells. Furthermore, by using time-lapse video microscopy it was possible to visualize an inducible array of transcription sites, mRNA synthesis and protein products in living cells[19]. Fourier spectroscopy-based spectral imaging (SIm) has been suggested for the quantitative analysis of RNA species[20]. Relative amounts of RNA were detected by hybridizing to six uniquely labeled cDNA probes specific for different tyrosine kinase genes and spectral images were analyzed using prerecorded reference spectra and deconvolution software. Quantitative fluorescence in situ hybridization (Q-FISH) in combination with flow cytometry, called Flow-FISH, has also been applied to the study of telomere lengths in leukemia cell lines using conditions optimized for routine and fast analysis[21].

Thus, the development of a highly sensitive, quantitative and multiplex system for gene and protein expression analysis in single cells remains an elusive goal for molecular research and diagnosis. Elemental analysis, combined with purpose-specific reagents, has the potential to achieve this goal.

Microspheres or beads are an attractive option for supporting surface chemistries of immunoassays. In a manner similar to 96 well plates, various compositions, coatings or conjugated groups can be constructed or added to provide the required surface chemistry. One of the advantages of microspheres is the ability to increase the reaction surface area per volume of the reaction mixture, which provides a reliable means of increasing the capacity and dynamic range potential of an immunoassay. In the following example, immunoassays were coupled with ICP-MS detection[22]. Flow cytometry initially developed for multiparametric cell analysis is also widely used to detect antigens and oligonucleotide probes conjugated to the surface of microspheres[23].

Conventional microsphere technology, based on fluorochrome emission detection, is thought to hold great promise as a tool to probe both genomic and proteomic function. Particle elemental analysis of uniquely labeled beads is poised to revolutionize gene expression studies, clinical diagnostics and cancer research. Polystyrene beads with embedded metals are coated with a thin polysilane layer to prevent elemental leaching commonly used in bonded-phase chromatography. Polystyrene beads are prepared according to conventional emulsion polymerization with styrene as monomer and potassium persulfate or benzoyl peroxide as polymerization agents. Allele-specific oligonucleotides (complementary probes) are covalently immobilized on the surface. Particles may carry 1 or more[8] different complementary oligonucleotide probes for the same gene. Hybridization is carried out with isolated mRNA or PCR products from a biological sample (target genes) to which element tags are added for target identification. Particles are subjected to flow-elemental analysis, for example flow-ICP-MS one by one to identify particle category and quantify the gene expression level. Microspheres imbibed with one element (Eu) and derivatized with carboxyl residues are available from Seradyn Inc. and are tested as proof of principle experiments in the applicant's teaching. The requirements for an elemental tag are relaxed in comparison to those for a fluorescent tag since the chemical nature of an element is not important for its detection by ICP-MS. A fundamental of the method requires that the element tags contain a reproducible and, preferably, large number of atoms of a given isotope. Reproducibility in the number of identical atoms incorporated is a basis for quantitative analysis, and an increase in the number of those atoms improves the sensitivity linearly.

A novel flow-based ICP-MS instrument may be used for gene expression profiling of single leukemia cells by particle elemental analysis. For this purpose abundant mRNA species may be detected by in situ hybridization. Multiplexing may be achieved by labeling oligonucleotide probes with different rare metal element tags that can be uniquely identified by the ICP-MS instrument. Sensitivity of RNA detection can be improved by using three to eight oligonucleotide probes per transcript and each probe labeled with multiple tags of a given element. Prior to multiplexing experiments with several genes, each transcript is hybridized separately to ensure that the level of expression is independent of multiplexing. An individual cell is estimated to express approximately 10,000 species of mRNA with the total RNA amount around 1-10 pg. Medium abundant transcripts range from 20 to 100 copies per cell, while highly abundant—more than 1000 copies of fusion transcripts in leukemia patient samples. Direct comparison of single-cell RNA profiling by flow-ICP-MS with previously performed microarray analysis may serve to validate the novel method. Selection of genes of interest may be performed with the help of publicly available databases such as NCBI, Integrated Molecular Analysis of Genomes and their Expression (IMAGE) Consortium and The Institute for Genomic Research. Furthermore, in situ hybridization using element tagged complimentary oligonucleotides and performed with homogeneous cell samples (cultured cell lines, leukemia samples from patients in blast crisis) may be analyzed by solution ICP-MS to determine the average gene expression profile averaged over the entire sample (schematic representation is given in FIG. 2A).

Ready made cDNA hybridization probes to some leukemia relevant genes (G-CSF receptor, Bax, Bcl-2, c-Fos, etc.) labeled with biotin can be obtained from commercial sources (Maxim Biotech Inc., GeneDetect Inc.) and research laboratories. Oligonucleotide probes are designed using software algorithms (commercial and publicly available) that select a sequence with optimal hybridization parameters as is known to those skilled in the art such as melting temperature (Tm), 50% G+C content, desired length of the probe. In the selection process an attempt is made to minimize the formation of hairpin structures and dimers between probes and decrease cross-homology with other target sequences. Oligonucleotides may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al.[24] In the applicant's teaching, carboxyl- or amino allyl-modified oligonucleotides may be attached to elemental tags or uniquely labeled supports, for example beads, through functional chemistry. Placing a functional group at the 5' end of the DNA strand and employing a suitable reagent to link the modified DNA to the surface of uniquely labeled supports, for example beads, will enable the covalent attachment of nucleic acids to supports. For example, to attach an amine-tagged DNA to carboxyl-modified particles, carbodiimide (EDC) chemistry may be used.

The invention provides for greater sensitivity and accuracy in the rapid analysis of hundreds of thousands of mRNA molecules. It further provides improved efficiency and accuracy of detection of gene expression levels by excluding fluorescent labeling of mRNA targets, at the same time ensuring a quantitative and high throughput measurement of RNA levels in a biological sample. The invention can also be used to detect other nucleic acids, for example, genomic DNA. For example, a single DNA strand is attached to an element tag on one end and the whole molecule is hybridized to a complementary oligonucleotide tethered to a uniquely labeled support (for example a bead).

SUMMARY

These and other features of the applicant's teachings are set forth herein.

In some embodiments a method of performing mass spectroscopy analysis using an inductively coupled plasma mass spectroscopy system is provided. The method may include introducing a cellular sample comprising one or more cells or cellular particles into an inductively coupled plasma of the inductively coupled plasma mass spectroscopy system. The method may further include using the inductively coupled plasma mass spectroscopy system to assess the cellular sample by detecting and measuring one or more element tags in the cellular sample based on the element or isotopic compositions of the one or more element tags.

In certain embodiments, the cellular sample may include first oligonucleotide probes each coupled with a first element tag. The first oligonucleotide probes may be hybridized with first target mRNA molecules of the cellular sample. The sample may further include affinity reagents each coupled with a second element tag having an elemental or isotopic composition different than the first element tag. The affinity reagents may be bound with cell surface proteins or intracellular protein molecules. Optionally, the method include using the inductively coupled plasma mass spectrometer to simultaneously assessing a protein expression level of the cellular sample and a gene expression level of the cellular sample by detecting and measuring the first element tags and the second element tags based on the element or isotopic compositions of the first and second elemental tags.

The cellular sample may be prepared by: rendering the first target mRNA molecules available for hybridization by at least one of fixing and permeabilizing the one or more cells or cellular particles; incubating the cellular sample with the affinity reagents under conditions to enable the affinity reagents to bind with the cell surface proteins or intracellular protein molecules; separating bound affinity reagents from unbound affinity reagents; incubating the cellular sample in a hybridization solution with the first oligonucleotide probes under conditions to enable the first oligonucleotide probes to hybridize preferentially to the first target mRNA molecules; and separating unhybridized first oligonucleotide probes from first oligonucleotide probes hybridized to the first target mRNA molecules.

In further embodiments, a method of using an elemental analyzer system for analysis of a cellular sample having a cell or cellular particle may be provided. The method may include rendering target nucleic acids available for hybridization to complementary oligonucleotide probes by chemically cross-linking cellular components of the cellular sample and creating holes in the cellular sample; incubating the cellular sample in a hybridization solution with oligonucleotide probes under conditions to enable the oligonucleotide probes to hybridize preferentially to the target nucleic acids through complementary base pairing between the oligonucleotide probes and the target nucleic acids; labeling the oligonucleotide probes with a unique element tag such that the oligonucleotide probes are distinguishable from any other type of oligonucleotide probes labeled with a different type of element tag by atomic composition analysis; separating unhybridized oligonucleotide probes from oligonucleotide probes hybridized to the target nucleic acid; analyzing an atomic composition of the cellular sample; analyzing gene expression of the cellular sample by detecting and measuring the unique element tags associated with the oligonucleotide probes of the cellular sample; and quantifying a gene expression level of the cellular sample based on the detection and measurement of the unique element tags.

An aspect of the applicant's teachings is to provide a method for cellular analysis, comprising: (a) providing a cell or a cellular particle; (b) fixing the cell or the cellular particle; (c) incubating the cell or the cellular particle in a hybridization solution with a probe specific for a target nucleic acid, the probe labeled with a unique element tag such that one type of said probe labeled with one type of said tag is distinguishable from any other type of said probe labeled with a different type of said tag by elemental analysis; (d) separating unhybridized probe from probe hybridized to the target nucleic acid by stringent washing conditions; and (e) analyzing the cell or cellular particle by elemental analysis to identify the probe and quantitate the probe bound to the target nucleic acid. Two or more differential probes labeled with differential element tags can be hybridized to two or more target nucleic acids. The target nucleic acid can be selected from the group consisting of intracellular nucleic acid molecules, matrix RNA, micro-RNA, gene transcript precursor RNA, messenger RNA, transport RNA, ribosomal RNA, chromosomal DNA, mitochondrial DNA, chloroplast DNA, viral DNA, viral RNA, bacterial DNA, bacterial RNA, and plasmid DNA. The method can further comprise simultaneous analysis of surface and/or intracellular protein molecules, surface and/or intracellular lipid molecules, surface and/or intracellular polysaccharide molecules, and/or surface and/or intracellular small molecules. The small molecules can be selected from the group consisting of vitamins, hormones, haptens and nucleosides (for example, ATP, ADP, cyclic AMP and NADH).

Further to the aspect above, the cell or cellular particle can be reacted with affinity reagents specific for surface or/and intracellular molecules, and the affinity reagents are labeled with element tags comprising a chemical moiety of a multitude of atoms of one or more isotopes of one or more elements attached to a supporting molecular structure, such that one type of said affinity reagent labeled with one type of said tag is distinguishable from any other type of said tag by elemental analysis, and followed by separating unbound affinity reagents from bound affinity reagents. The surface or/and intracellular molecules can be proteins, lipids, polysaccharides and/or small molecules. The affinity reagents can be selected from the group consisting of antibodies, aptamers, lectins and small molecules. The cell can be a whole cell of an animal, plant, bacterium or fungus. The cellular particle can be selected from the group consisting of an isolated chromosome, an isolated nucleus, an isolated mitochondria, an isolated chloroplast, an isolated virus, and an isolated bacterium. The probe can be selected from the group consisting of an oligonucleotide probe, a locked nucleic acid (LNA) molecule, a peptide nucleic acid (PNA) molecule, a plasmid DNA, an amplified DNA, an amplified, a fragment of RNA and a fragment of genomic DNA.

Another aspect of the applicant's teachings is to provide a method for homogeneous analysis of biological molecules, comprising: (a) incubating biological molecules with affinity reagents labeled with element tags and uniquely tagged particles such that one type of said particles labeled with one type of said tags is distinguishable from any other type of said particle labeled with a different type of said tags by elemental analysis, under conditions to enable the affinity reagents to bind with the biological molecules; (b) separating the particles with bound biological molecules from unbound particles; (c) measuring the bound particles by particle elemental analysis wherein the particles are dispersed in a liquid to measure quantitatively the atomic and isotopic composition of individual particles, thereby detecting the types and the numbers of biological molecules attached to said particles. The particles can be beads. The biological molecules can be from a tissue or a cell sample. The sample can be selected from the group consisting of an animal sample, a plant sample, a bacterium sample, and a fungal sample. The biological molecules can be selected from the group consisting of mRNA, protein, lipids, polysaccharides and small molecules. The binding of biological molecules with affinity reagents can comprise the hybridization of mRNA molecules with oligonucleotides attached to uniquely tagged microspheres. The oligonucleotides can comprise of a number of deoxythimidine triphosphate nucleosides. And complementary nucleic acid probes attached to uniquely tagged microspheres. The complementary nucleic acid probes can be selected from the group consisting of oligonucleotides, LNA, PNA and plasmid DNA. The biological molecules can be selected from the group consisting of proteins, lipids, polysaccharides and small molecules and they bind with elemental tagged affinity reagents bound to uniquely tagged microspheres. The affinity reagents can be selected from the group consisting of antibodies, aptamers, and lectins, nucleic acids, binding peptides, protein receptors, and phospholipids.

Another aspect of the applicant's teachings is a kit for the detection and measurement of an element in a sample, where the measured element is an element tag attached to a specific probe complementary to a nucleic acid of interest, comprising: (a) an element tag for directly tagging a complementary probe; and (b) a complementary probe. The kit can further comprise instructions for i) direct tagging of the probe with the element tag; ii) fixing and permeabilizing a cell or cellular particle; iii) incubating the cell or cellular particle with the element tagged probe in a hybridization solution; iv) separating bound probe from unbound probe; v) dissolving the cell or cellular particle with hybridized material, and vi) detecting and measuring the element tagged probe. The detecting and measuring can be done by volume elemental analysis or particle elemental analysis.

Another aspect of the applicant's teachings is to provide a kit for the detection and measurement of an element in a sample, where the measured element is an element tag attached to a specific probe complementary to a nucleic acid of interest, comprising: (a) a complementary probe tagged with an element tag. The kit can further comprising instructions for i) fixing and permeabilizing a cell or cellular particle; ii) incubating the cell or cellular particle with the element tagged probe in a hybridization solution; iii) separating bound probe from unbound probe; iv) dissolving the cell or cellular particle with hybridized material, and v) detecting and measuring the element tagged probe.

The kits described above can further comprise a multitude of specific probes complementary to a multitude of nucleic acids and a multitude of unique element tags for uniquely labeling each type of probe. The kits described above can further comprise (a) an affinity reagent for an intra or extracellular biological molecule selected from the group consisting of a protein, a lipid, a polysaccharide and a small molecule; and (b) an elemental tag for labeling the affinity reagent for the biological molecule. The kits can comprise instructions for (i) tagging the affinity reagent for the biological molecule, (ii) incubating the cell or cellular particle with the affinity reagent for the biological molecule; (iii) separating bound affinity reagent for the biological molecule from unbound reagent for the biological molecule; and (iv) detecting and measuring the bound reagent for the biological molecule. Finally, the kits can comprise a multitude of specific reagents for a multitude of biological molecules and a multitude of elemental tags for uniquely labeling each type of affinity reagent for each type of biological molecule.

Another aspect of the applicant's teaching is to provide a kit for the detection and measurement of an element, where the measured element is an element tag attached to oligo (dT)n which is attached to distinguishable element labeled particles, comprising: (a) an element tag for directly tagging oligo(dT)n; (b) oligo(dT)n; (c) a multitude of distinguishable element labeled particles; and (d) a multitude of complementary probes. The kit can further comprise instructions for i) directly attaching the multitude of complementary probes to distinguishable element labeled particles; ii) performing nucleic acid purification; (iii) attaching the element tag to the oligo(dT)n; iv) reacting the complementary probes with the element tagged oligo(dT)n; v) hybridizing the complementary probes attached to element tagged oligo (dT)n which are attached to distinguishable element labeled particles in a solution with a target nucleic acid; vi) separating bound particles from unbound particles; vii) detecting and measuring the bound particles by particle elemental analysis. The particles can be beads. The multitude of complementary probes can be directly tagged with distinguishable elemental tags.

Another aspect of the applicant's teachings is to provide kit for the detection and measurement of an element, where the measured element is an element tag attached to oligo (dT)n which is attached to distinguishable element labeled particles, comprising: (a) an element tag for directly tagging oligo(dT)n; (b) oligo(dT)n; and (c) a multitude of complementary probes attached to a multitude of distinguishable element labeled particles. The kit can further comprise instructions for i) performing nucleic acid purification; (ii) attaching the element tag to the oligo(dT)n; iii) reacting the complementary probes with the element tagged oligo(dT)n; iv) hybridizing the complementary probes attached to element tagged oligo(dT)n which are attached to distinguishable element labeled particles in a solution with a target nucleic acid; v) separating bound particles from unbound particles; vi) detecting and measuring the bound particles by particle elemental analysis.

Another aspect of the applicant's teachings is a kit for the detection and measurement of an element, where the measured element is an element tag attached to oligo(dT)n and elements of uniquely labeled particles attached to a complementary probe, comprising: (a) an element tag labeled oligo(dT)n; and (b) a multitude of complementary probes attached to a multitude of uniquely labeled particles. The kit further comprises instructions for i) performing nucleic acid purification; ii) hybridizing the complementary probes attached to uniquely labeled particles with purified nucleic acid; iii) reacting uniquely labeled particles with the metal tagged oligo(dT)n; iv) separating bound particles from unbound particles; v) detecting and measuring the elements of bound particles by particle elemental analysis.

In a further aspect, the particle can be replaced by a solid support. For example the support could be a flat (for example glass or plastic) plate, a well-plate, a probe (inserted into the sample) or other solid material. In this instance, the solid surface does not necessarily have to be element-labeled, since the position (on a plate or well plate) could indicate the identity of the complementary probe that is attached thereto. The instructions would be similar to (i) through (v) described above, but in this case only the element attached to the oligo(dT)n is measured.

The kits described above can further comprise reagents and devices selected from the group consisting of dissociation solutions, spin columns with nucleic acid binding membranes, purification column for isolation and purification of nucleic acids from biological samples, reagents and solutions for amplification of purified nucleic acids, standards, dilution buffer, dissociation buffer, wash buffer, hybridization buffer and assay buffer. Endogenous nucleic acids can be in situ amplified in morphologically intact cells. The element can be measured using a mass spectrometer. The element can be an isotope or ion. The element can be selected from a group consisting of the transition elements, noble metals, lanthanides, rare earth elements, gold, silver, platinum, rhodium, iridium and palladium. The element can include more than one element and/or more than one isotope and/or more than one atom of an isotope. The affinity products can be selected from the group consisting of antibody, Fab', aptamer, antigen, hormone, growth factor, receptor, protein and nucleic acid. The kits can also include instruction for particle elemental analysis.

BRIEF DESCRIPTION OF THE FIGURES

The skilled person in the art will understand that the figures, described below, are for illustration purposes only. The figures are not intended to limit the scope of the applicant's teaching in any way. The invention is illustrated in the figures, which are meant to be exemplary and not limiting.

DETAILED DESCRIPTION OF THE FIGURES

Figure 1A:
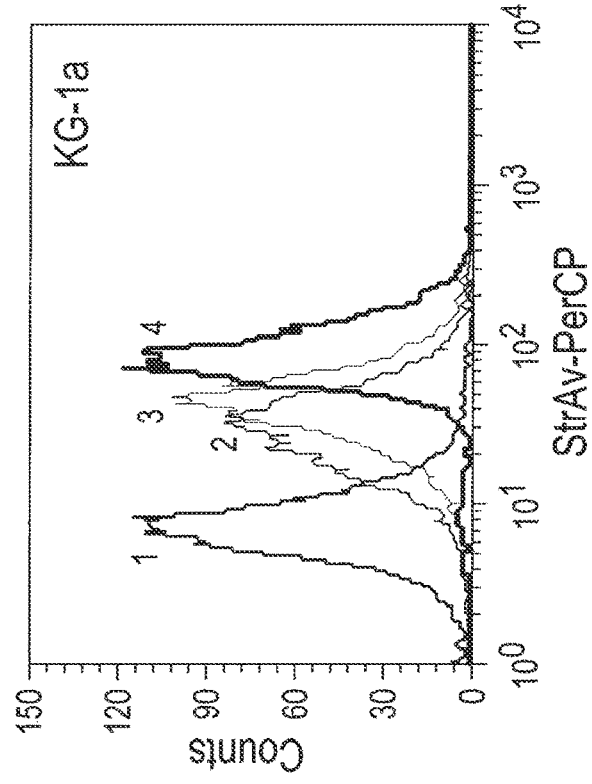
FIG. 1A shows an in situ hybridization and flow cytometry detection of 28S rRNA using biotinylated antisense oligonucleotides ("oligos") in three different conditions.
Figure 1B:
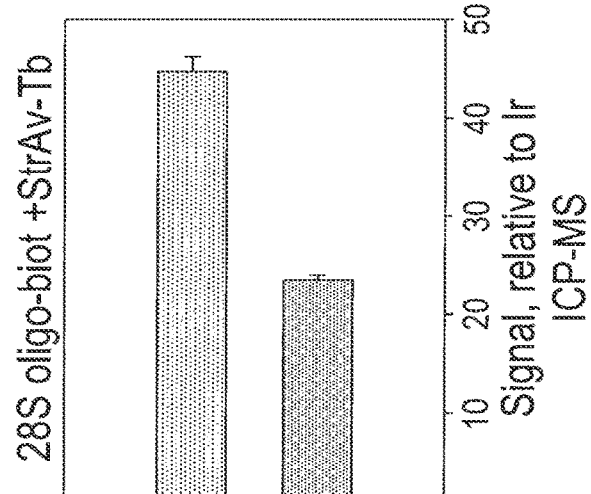
FIG. 1B shows a comparison of 28S rRNA in situ hybridization analyzed by flow cytometry (left graph) and ICP-MS (right graph)

FIG. 1A. In situ hybridization and flow cytometry detection of 28S rRNA using biotinylated antisense oligonucleotides ("oligos") in three different conditions. (1)—corresponds to negative control cells hybridized with a nonsense biotinylated oligonucleotide ("oligo"), (2)—cells fixed with 4% para-formaldehyde 15 minutes, followed by Proteinase K (5 U/ml) for 15 minutes at room temperature and hybridized with 28S rRNA oligo; (3)—cells treated with 4% para-formaldehyde 15 minutes and Proteinase K (5 U/ml) for 15 minutes at 37° C. and hybridized with 28S rRNA oligo; (4)—cells fixed with 4% para-formaldehyde 15 minutes, followed by 0.3% Triton-X100, followed by Proteinase K (5 U/ml) for 15 minutes at 37° C. and hybridized with 28S rRNA oligo. Conditions denoted by (4) were chosen for further experiments. FIG. 1B. Comparison of 28S rRNA in situ hybridization analyzed by flow cytometry (left graph) and ICP-MS (right graph).

FIG. 2. BCR/Abl (Break point cluster region/Abelson leukemia) gene expression analysis in leukemia cells by ICP-MS. (A) Schematic in situ hybridization of fixed/permeabilized cells with a biotinylated oligonucleotide probe for BCR/Abl fusion gene. Biotin is identified by streptavidin (StrAv) labeled with terbium (Tb). Cell pellet is dissolved in HCL and analyzed by solution elemental ICP-MS analysis. (B) Experimental results for KG-1a cells (left graph) and K562 cells (right graph), hybridized with BCR/Abl antisense, 28S rRNA (positive control) and non-sense oligo probes (B/A) and no probe (ctrl); background and non-sense probe response values subtracted. Samples were run in triplicate. Data are presented as normalized ratio of terbium (Tb) to iridium (Ir) internal standard signal.

Figure 3:
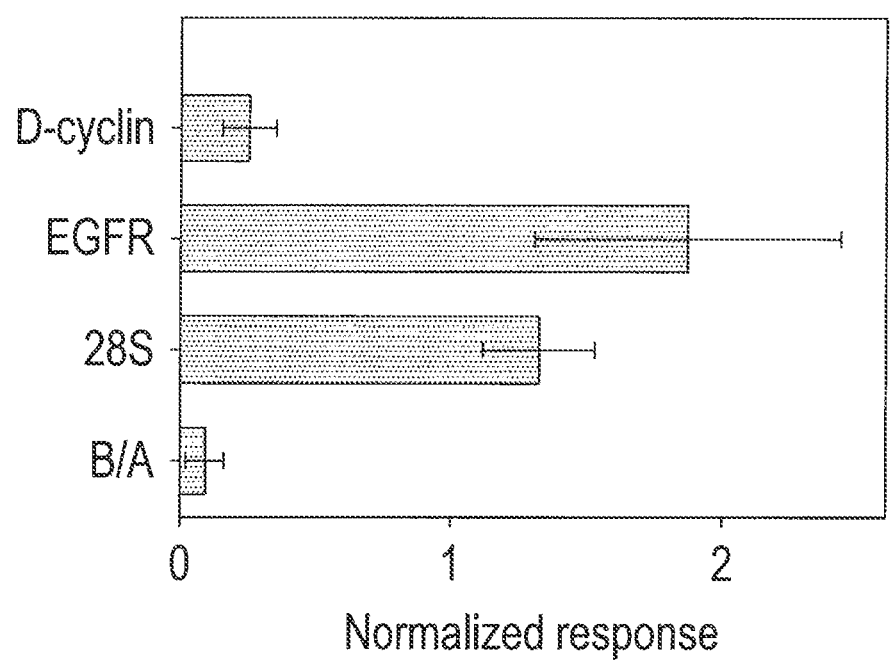
FIG. 3 shows an epidermal growth factor receptor (EGFR) gene expression analysis in adherent carcinoma cells by ICP-MS.

FIG. 3. Epidermal growth factor receptor (EGFR) gene expression analysis in adherent carcinoma cells by ICP-MS. A431 cells were hybridized with gene specific probes to EGFR, D-cyclin, 28S rRNA (positive control), and non-sense negative control, B/A. (B/A is a random oligo with random name used as negative control) Samples were run in triplicate. Data are presented as normalized ratio of terbium (Tb) to iridium (Ir) internal standard signal.

FIG. 4. Simultaneous protein and gene expression analysis in K562 leukemia cells by ICP-MS. (A) In situ hybridization with 28S rRNA and non-sense oligo probes (B/A); (B) immunolabeling of BCR/Abl protein and negative control IgG values during hybridization. Samples were run in triplicate. Data are presented as normalized ration of europium (Eu) or terbium (Tb) to iridium (Ir) internal standard signal.

Figure 5:
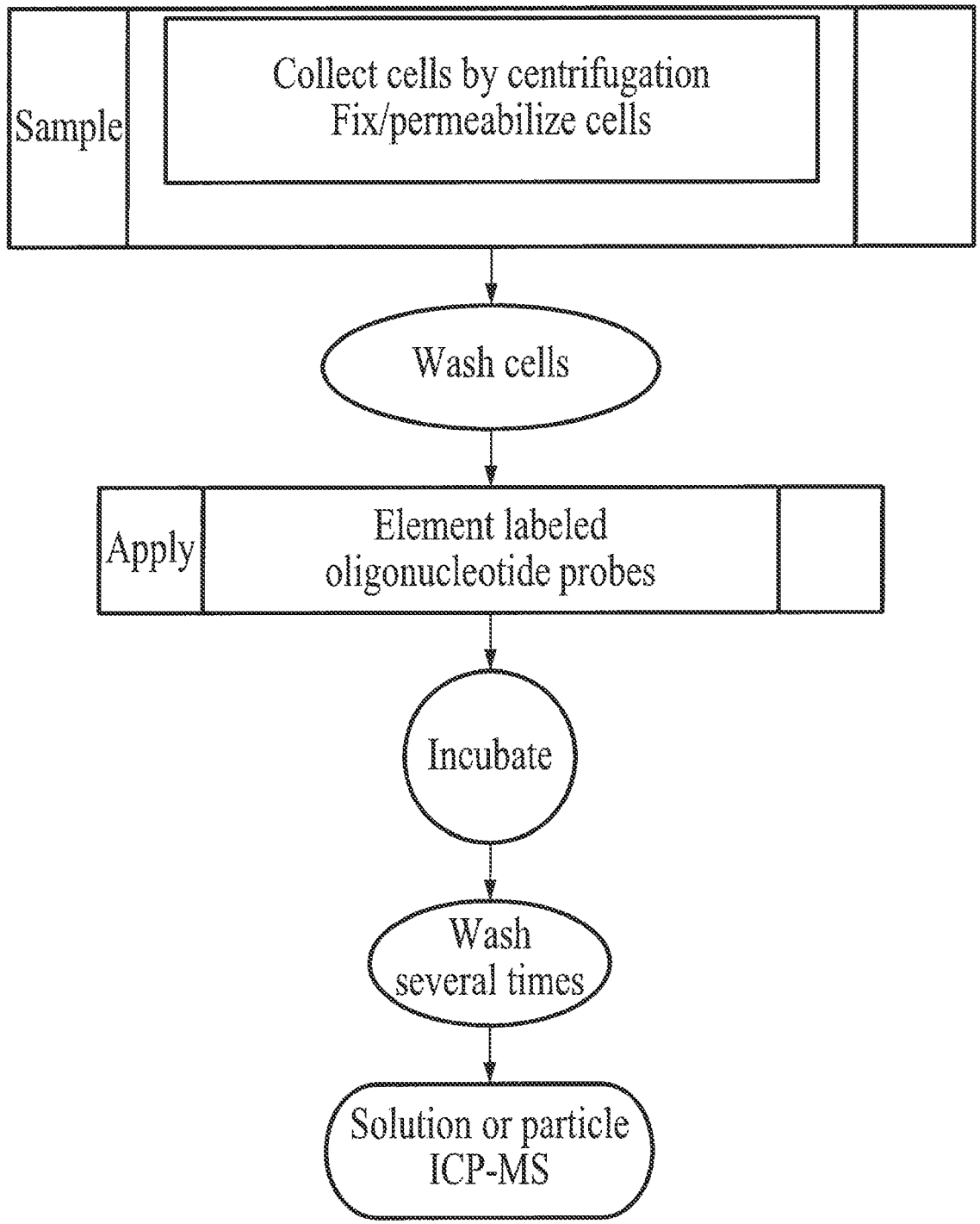
FIG. 5 shows a work flow chart for in situ hybridization and gene expression analysis by ICP-MS.

FIG. 5. Work flow chart for in situ hybridization and gene expression analysis by ICP-MS.

Figure 6:
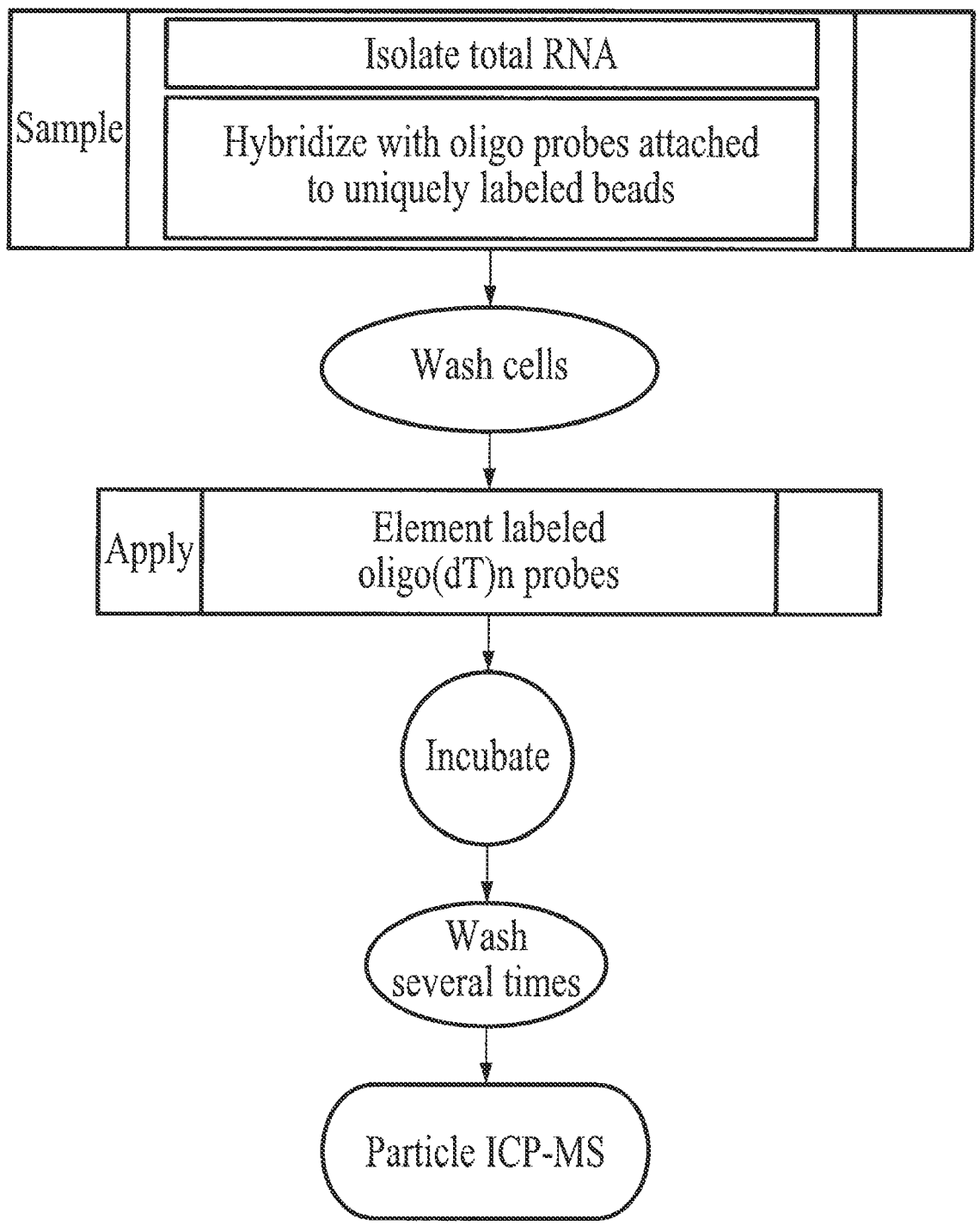
FIG. 6 shows a work flow chart for element labeled bead gene expression analysis by particle elemental analysis.

FIG. 6. Work flow chart for element labeled bead gene expression analysis by particle elemental analysis.

Figure 7:
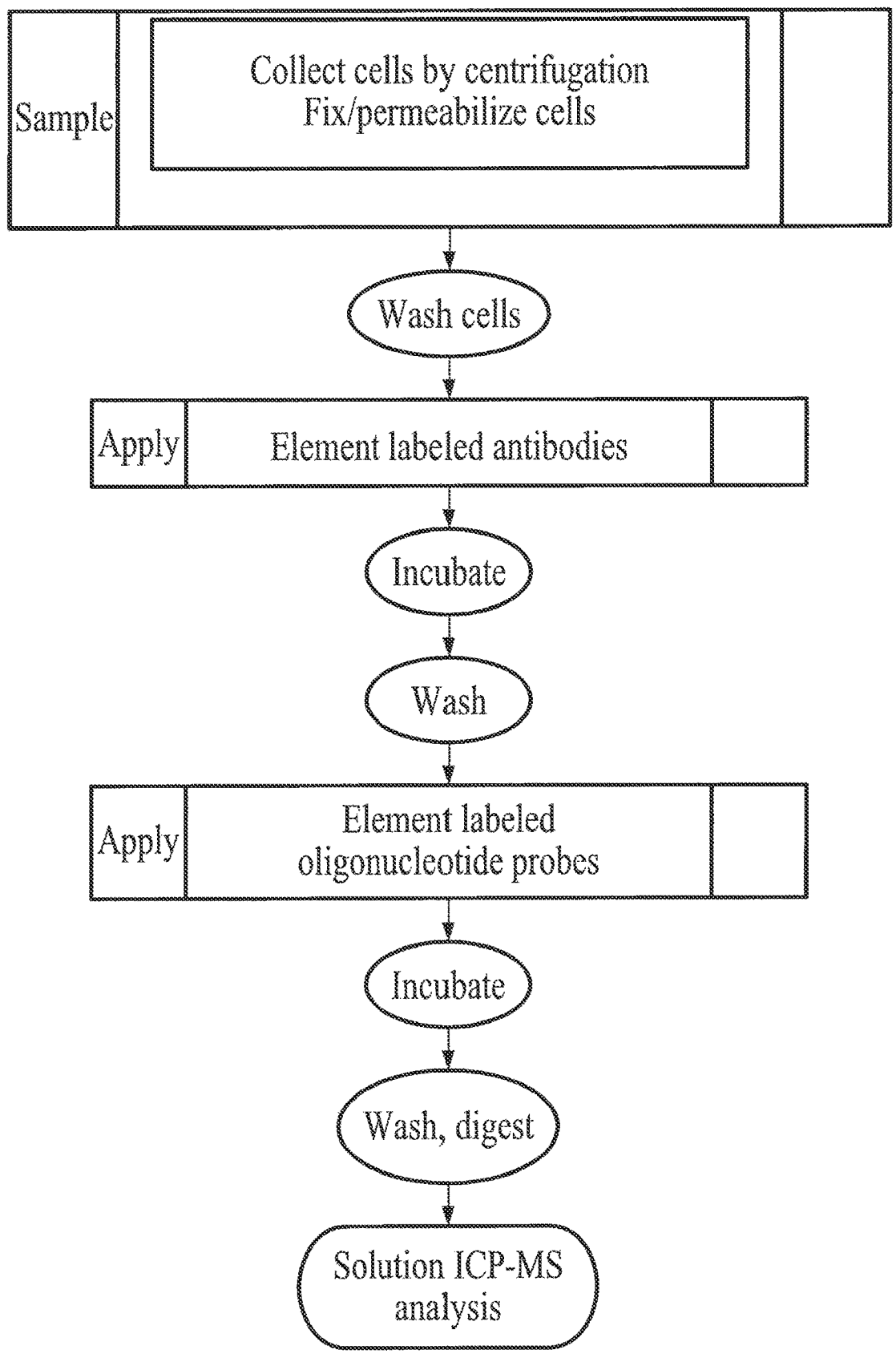
FIG. 7 shows a work flow chart for simultaneous gene and protein expression analysis by ICP-MS.

FIG. 7. Work flow chart for simultaneous gene and protein expression analysis by ICP-MS.

DESCRIPTION OF VARIOUS EMBODIMENTS

The present invention comprises use of elemental tags. The choice of the element to be employed in the methods of the applicant's teaching is preferably selected on the basis of its natural abundance in the sample under investigation and whether the element is toxic to the sample under investigation.

Most metals of the transition and rare earth groups are anticipated for use in the applicant's teaching. It is wise to choose elements that have low or no cytotoxicity and have a low abundance in growth media and biological samples. For example, vanadium and mercury can be toxic to certain cells, while Fe, Cu and Zn can be present in high concentrations in some cell culture media. On the other hand, Pr, Ho, Tb, La, for example are normally well tolerated by mammalian cells and are not abundant in the environment.

An unusual isotope composition of the tag element can be used in order to distinguish between naturally present elements in the sample and the tag material. It is advantageous if the relative abundance of the tag elements is sufficiently different from the relative abundance of elements in a given sample under analysis. By "sufficiently different" it is meant that under the methods of the present invention it is possible to detect the target elemental tag over the background elements contained in a sample under analysis. Indeed, it is the difference in inter-elemental ratios of the tagging elements and the sample matrix that can be used advantageously to analyze the sample.

It is feasible to select elemental tags, which do not produce interfering signals during analysis (i.e. do not have over-lapping signals due to having the same mass). Therefore, two or more analytical determinations can be performed simultaneously in one sample. Moreover, because the elemental tag can be made containing many copies of the same atoms, the measured signal can be greatly amplified.

Aspects of the applicant's teachings may be further understood in light of the following examples, which should not be construed as limiting the scope of the present teachings in any way.

Experiment 1

In one embodiment, wherein the work flow chart is presented in FIG. 5, in situ hybridization for ICP-MS detection is performed by first treating the tissue or cell sample in such a way as to render target chromosomal and extrachomasomal nucleic acids available for hybridization to complementary probes (fixation/permeabilization); then exposing the sample to a probe or multiple probes labeled with different elemental tags and complementary to genes of interest; thirdly, washing sample to eliminate excess unbound and non-specifically interacting probe; finally subjecting the sample to particle or solution elemental analysis.

Experiment 2

For element labeled bead gene analysis by ICP-MS (work flow chart shown in FIG. 6), total RNA is isolated from a biological sample and is hybridized with uniquely labeled beads conjugated to oligonucleotide probes; elemental tagged oligo(dT)20 probe; are added to the mixture; finally, the beads are subjected to single particle ICP-MS analysis.

Total RNA is isolated from a given sample using methods known in the art. For example, an acid guanidinium-phenol-chloroform extraction method can be used or a commercial reagent such as TRizol Reagent (GIBCOL Life Technologies) can be used for isolation of RNA from mammalian tissue. Additionally, messenger RNA may be isolated by oligo dT column chromatography or by using (dT)n magnetic beads (see, e.g., Sambrook et al.[25], F. Ausubel et al.[26]). Conveniently, total RNA can be isolated from mammalian cells using RNeasy Total RNA isolation kit, for example (QIAGEN). A second cleanup after the ethanol precipitation step in the TRizol extraction using Rneasy total RNA isolation kit may be beneficial. One round of RNA amplification may be required (Ambion kit). It will be appreciated by one of skill in the art that this provides an antisense (aRNA) pool. Where antisense RNA is used as the target nucleic acid, the oligonucleotide probes are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be either sense or antisense as the target nucleic acids include both sense and antisense strands.

Expression level controls are probes that hybridize specifically with constitutively expressed genes in the biological sample and are used for normalization. Virtually any constitutively expressed gene provides a suitable target for expression level controls. Typically expression level control probes have sequences complementary to subsequences of constitutively expressed "house-keeping genes" including, but not limited to the beta-actin gene, the transferring receptor gene, the GAPDH gene, HPRT, CPB, G6PD, 28S rRNA and the like.

The method of the invention can be used for nucleic acid detection, together with protein detection for the identification of bacteria, forensic science and simultaneous gene and protein expression analysis.

The method can also use a support as is known to those skilled in the art, for example a slide, plate or well, in place of the beads or particles.

In a variation of this method, biological molecules (for example but not limited to, proteins, lipids, polysaccharides), bind specific small molecules (for example but not limited to, drugs, hormones, pheromones, sugars) that are labeled with elemental tags which bind uniquely tagged supports coated with 'affinity reagents' against the biological molecules. The supports are then analyzed by elemental analysis to identify the reaction of said biological molecules with the small molecules (for example, as in receptor binding a growth factor). In this instance the small molecules are tagged directly and recognition of the small molecule analytes is by virtue of their binding, via an affinity reagent to an element-labeled bead, and the concomitance of the bead elemental signature with the small molecule's tag signature confirms and quantifies the small molecule.

Experiment 3

In yet another embodiment, the first series of examples were performed using conventional ICP-MS instrumentation as a detector and commercial metal (lanthanide) containing affinity reagents. It is to be understood that other metals can be used and that other instrumentation for elemental analysis can be used. Experiments employing biotinylated antisense oligonucleotide probes designed to hybridize in situ to specific, disease-relevant genes in human leukemia cells were used. The probes were identified by association with lanthanide labeled streptavidin (see FIG. 2A).

Figure 1B:
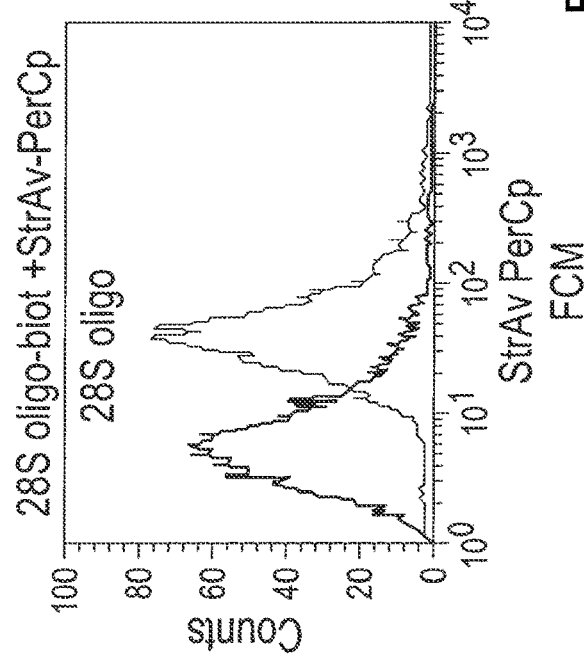

The feasibility of performing in situ hybridization with ICP-MS detection was tested on a model human leukemia cell line and results were compared to flow cytometry as shown in FIG. 1. Experiments were carried out to define the optimal fixation and permeabilization conditions and in situ hybridization parameters for suspension cells which were subsequently used for ICP-MS gene expression analysis. KG-1A cells were fixed as indicated in FIG. 1 (legend) and then incubated in hybridization solution with 500 ng/ml of biotinylated 28S rRNA probe (5'-biotin-ATCCAACGCT-TGGTGAATTC-3' (SEQ ID NO.1), human 28S ribosomal RNA GI:337381) or a non-sense biotinylated probe (B/A; negative control). Following washing and blocking, streptavidin-PerCP (streptavidin labeled with peridin chlorophyll-a protein) was added. FIG. 1A shows histograms of fluorescence intensity obtained on a FACSCalibur (BD Biosciences) flow cytometer. FIG. 1B shows an ICP-MS volume bulk analysis: hybridized cells were reacted with streptavidin-Tb (DELFIA), washed and dissolved in concentrated HCl with 1 ppb Ir (iridium internal standard). There is a clear hybridization signal for human 28S rRNA detected by both flow cytometry (FCM) and ICP-MS. Thus, using secondary affinity reagents labeled with metal (streptavidin-Tb) experimental conditions were established for successfully identifying highly abundant constitutive transcripts in leukemia cells by ICP-MS.

Experiment 4

Figure 2A:
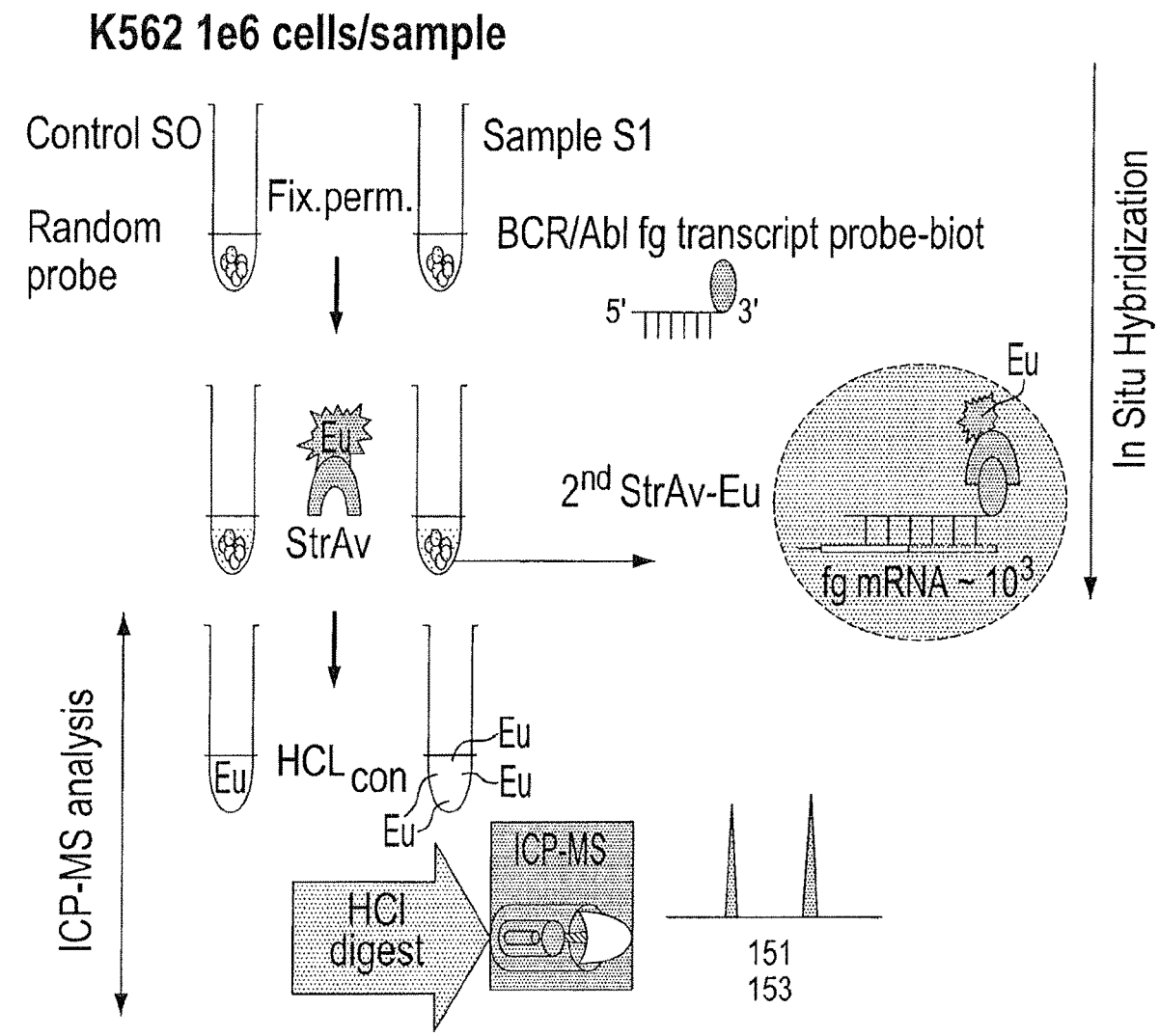
FIG. 2A shows a schematic in situ hybridization of fixed/permeabilized cells with a biotinylated oligonucleotide probe for BCR/Abl fusion gene.
Figure 2B:
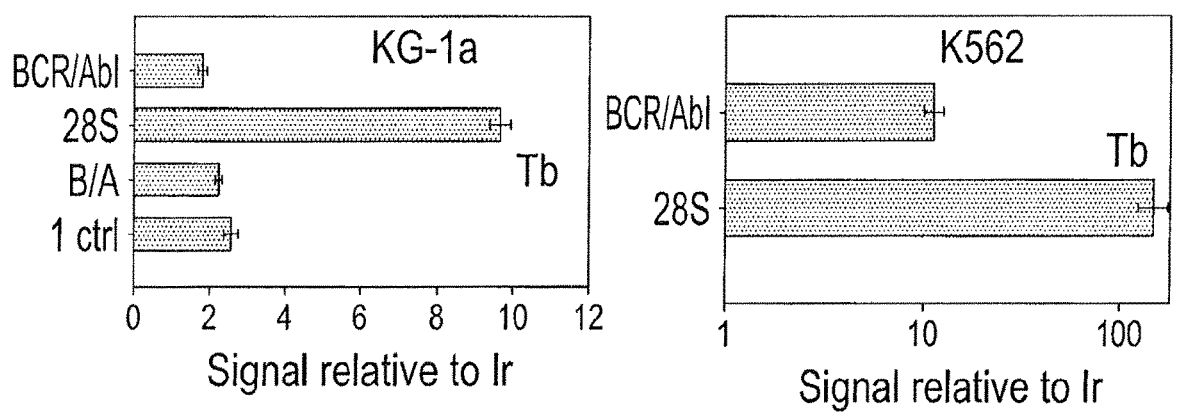
FIG. 2B shows experimental results for KG-1a cells (left graph) and K562 cells (right graph)

The next embodiment demonstrates that in situ hybridization with ICP-MS detection is sensitive enough to detect moderately abundant leukemia-specific gene species. For this purpose a human chronic myeloid leukemia cell line (K562), which is known to express the BCR/Abl oncogenic kinase encoded by the b3a2 gene, and antisense oligonucleotides were used. A schematic for the experiment is shown in FIG. 2A. We compared the expression of b3a2 fusion gene in K562 cells and KG-1A cells (acute myeloid leukemia model cell line; does not express BCR/Abl transcript) using a 5'-biotinylated BCR/Abl-specific antisense probe (BCR/Abl), a 5'-biotinylated 28S rRNA probe (positive control) and a biotinylated non-sense probe (B/A). Cells were fixed and permeabilized as described in FIG. 1, then separate cell samples were incubated in hybridization solution containing either biotinylated BCR/Abl, 28S rRNA, non-sense probes or no probe. Following washing and blocking, streptavidin-Tb was added. Analysis was done by solution elemental analysis where labeled cells were dissolved in HCl/Ir and the entire sample (0.3e6 KG1a cells and 3e6 K562 cells per sample) was subjected to elemental analysis by a conventional ICP-MS instrument. Results are presented in FIG. 2B. The graph on the left demonstrates that while the level of 28S rRNA in KG-1A cells is very high, the signal from BCR/Abl probe is at the levels of non-sense (B/A) and negative control (ctrl) responses. On the other hand, K562 cells (right graph in FIG. 2B) hybridize strongly with the BCR/Abl probe, approximately 14-fold lower than with 28S rRNA. Thus, ICP-MS reliably detects BCR/Abl gene levels in K562 cells.

Experiment 5

Yet in another embodiment in situ hybridization experiment was done using adherent A431 human epidermoid carcinoma cells. These cells are known to overexpress epidermal growth factor receptor (EGFR). Cells were seeded into tissue culture grade 96-multiwell plates and allowed to attach and proliferate for two days (~75e3 cells per well). The cells were fixed and permeabilized according to method (4) in legend of FIG. 1.; washed and hybridized with antisense oligonucleotide probes 5'-labeled with biotin: 28S rRNA, EGFR, D-cyclin and B/A in the wells. Triplicate wells were set up for each probe. The probes were reacted with streptavidin-Tb. After washing, cells were dissolved in HCL/Ir and analyzed by solution ICP-MS. As evident from FIG. 3, A431 cells express a high amount of EGFR mRNA, substantially lower levels of D-cyclin (not all cells were proliferating) and show a robust response for the positive probe, 28S rRNA.

Experiment 6

Figure 4A:
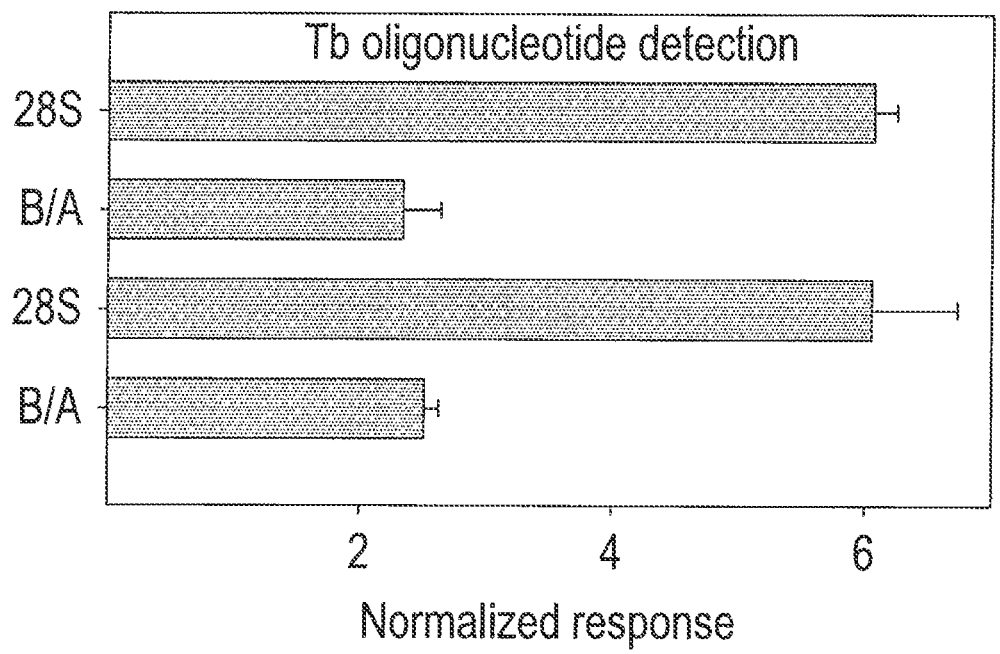
FIG. 4A shows in situ hybridization with 28S rRNA and non-sense oligo probes.
Figure 4B:
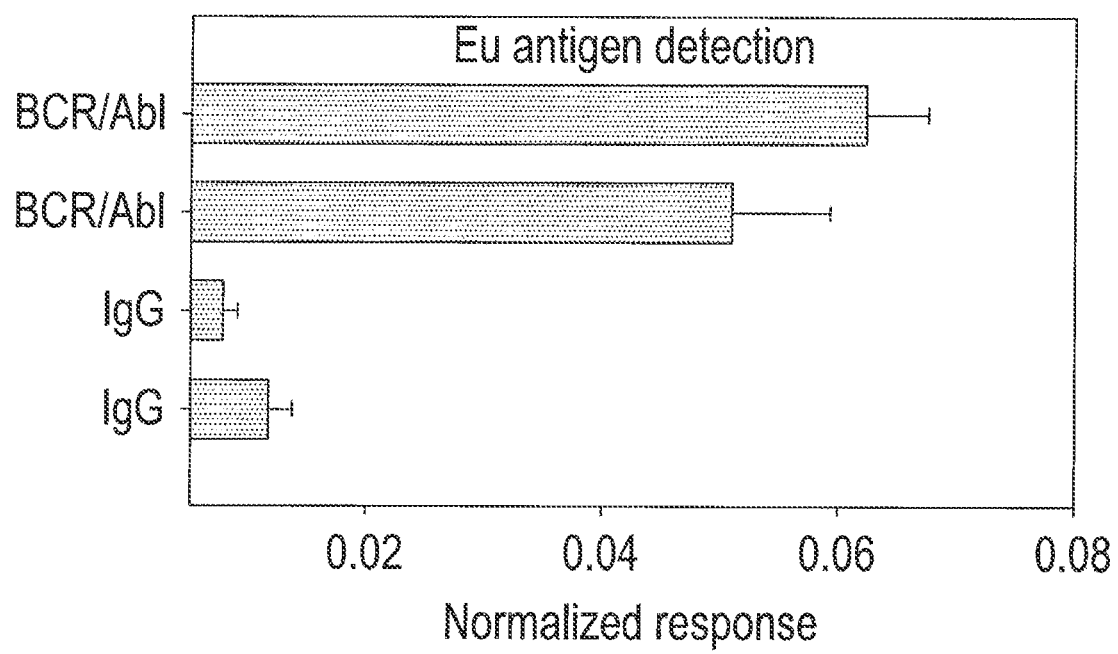
FIG. 4B shows immunolabeling of BCR/Abl protein and negative control IgG values during hybridization.

The following experiment illustrates the unique capability of the applicant's teachings to simultaneously detect protein and gene expression in the same cells (see FIG. 7). For this purpose we used the K562 model cell line, which expresses high levels of p210 BCR/Abl protein. Primary antibody that recognizes BCR/Abl protein (Cell Signaling Technol., Inc.) or isotype control IgG were applied to cells fixed and permeabilized in PermFlow solution (InVirion, Inc.). Cells were then washed with PBS and reacted with secondary anti-rabbit-Eu conjugate (DELFIA, Perkin Elmer) (see FIG. 4B). Following immunolabeling cells were prehybridized in DAKO In situ Hybridization solution (DAKO, Inc.) and hybridized with the 5'-biotinylated-28S ribosome RNA antisense probe or with the 5'-biotinylated-B/A non-sense probe as negative control for 2 hours at room temperature. Stringent washes with 4×SSC, 2×SSC, 0.2×SSC and PBS were performed to minimize non-specific hybridization. Finally, the cells were incubated with streptavidin-Tb conjugate (DELFIA) and dissolved in HCl/Ir (FIG. 4A). As evident from comparing FIG. 4A and FIG. 4B, cells stained for BCR/Abl protein expression (Eu) and probed for ribosomal gene expression (Tb) gave significantly higher signals than cells stained for IgG control and B/A probe.

Kits:

The invention also provides kits comprising components to practice the methods of the invention.

For example, a kit is provided for the detection and measurement of an element in a sample, where the measured element is an element tag attached to a specific probe complementary to a nucleic acid of interest, comprising: (a) an element tag for directly tagging a complementary probe; and (b) a complementary probe. The kit can further comprise instructions for i) direct tagging of the probe with the element tag; ii) fixing and permeabilizing a cell or cellular particle; iii) incubating the cell or cellular particle with the element tagged probe in a hybridization solution; iv) separating bound probe from unbound probe; v) dissolving the cell or cellular particle with hybridized material, and vi) detecting and measuring the element tagged probe. The detecting and measuring can be done by solution elemental analysis or particle elemental analysis.

A kit is also provided for the detection and measurement of an element in a sample, where the measured element is an element tag attached to a specific probe complementary to a nucleic acid of interest, comprising: (a) a complementary probe tagged with an element tag. The kit can further comprising instructions for i) fixing and permeabilizing a cell or cellular particle; ii) incubating the cell or cellular particle with the element tagged probe in a hybridization solution; iii) separating bound probe from unbound probe; iv) dissolving the cell or cellular particle with hybridized material, and v) detecting and measuring the element tagged probe.

The kits described above can further comprise a multitude of specific probes complementary to a multitude of nucleic acids and a multitude of unique element tags for uniquely labeling each type of probe. The kits described above can further comprise (a) an affinity reagent for an intra or extracellular biological molecule selected from the group consisting of a protein, a lipid, a polysaccharide and a small molecule; and (b) an elemental tag for labeling the affinity reagent for the biological molecule. The kits can comprise instructions for (i) tagging the affinity reagent for the biological molecule, (ii) incubating the cell or cellular particle with the affinity reagent for the biological molecule; (iii) separating bound affinity reagent for the biological molecule from unbound reagent for the biological molecule; and (iv) detecting and measuring the bound reagent for the biological molecule. Finally, the kits can comprise a multitude of specific reagents for a multitude of biological molecules and a multitude of elemental tags for uniquely labeling each type of affinity reagent for each type of biological molecule.

Another kit is provided for the detection and measurement of an element, where the measured element is an element tag attached to oligo(dT)n and elements of uniquely labeled particles, comprising: (a) an element tag for directly tagging oligo(dT)n; (b) oligo(dT)n; (c) a multitude of uniquely labeled particles; and (d) a multitude of complementary probes. The kit can further comprise instructions for i) directly attaching the multitude of complementary probes to uniquely labeled particles; ii) performing nucleic acid purification; iii) attaching the element tag to the oligo(dT)n; iv) hybridizing the complementary probes attached to uniquely labeled particles with purified nucleic acid; iii) reacting bound uniquely labeled particles with the metal tagged oligo(dT)n; iv) separating bound particles from unbound particles; v) detecting and measuring the elements of bound particles by particle elemental analysis. The particles can be beads. In a further aspect, the particle can be replaced by a solid support. For example the support could be a flat (for example glass or plastic) plate, a well-plate, a probe (inserted into the sample) or other solid material. In this instance, the solid surface does not necessarily have to be element-labeled, since the position (on a plate or well plate) could indicate the identity of the complementary probe that is attached thereto. The instructions would be similar to (i) through (v) described above, but in this case only the element attached to the oligo(dT)n is measured.

Another kit is provided for the detection and measurement of an element, where the measured element is an element tag attached to oligo(dT)n which is attached to distinguishable element labeled particles, comprising: (a) an element tag for directly tagging oligo(dT)n; (b) oligo(dT)n; and (c) a multitude of complementary probes attached to a multitude of distinguishable element labeled particles. The kit can further comprise instructions for i) performing nucleic acid purification; (ii) attaching the element tag to the oligo(dT)n; iii) reacting the complementary probes with the element tagged oligo(dT)n; iv) hybridizing the complementary probes attached to element tagged oligo(dT)n which are attached to distinguishable element labeled particles in a solution with a target nucleic acid; v) separating bound particles from unbound particles; vi) detecting and measuring the bound particles by particle elemental analysis.

In a further aspect, the particle can be replaced by a solid support. For example the support could be a flat (for example glass or plastic) plate, a well-plate, a probe (inserted into the sample) or other solid material. In this instance, the solid surface does not necessarily have to be element-labeled, since the position (on a plate or well plate) could indicate the identity of the complementary probe that is attached thereto. The instructions would be similar to (i) through (v) described above, but in this case only the element attached to the oligo(dT)n is measured.

The kits described above can further comprise reagents and devices selected from the group consisting of dissociation solutions, spin columns with nucleic acid binding membranes, purification column for isolation and purification of nucleic acids from biological samples, reagents and solutions for amplification of purified nucleic acids, standards, dilution buffer, dissociation buffer, wash buffer, hybridization buffer and assay buffer. Endogenous nucleic acids can be in situ amplified in morphologically intact cells. The element can be measured using a mass spectrometer. The element can be an isotope or ion. The element can be selected from a group consisting of the noble metals, lanthanides, rare earth elements, gold, silver, platinum, rhodium, iridium and palladium. The element can include more than one element and/or more than one isotope and/or more than one atom of an isotope. The affinity products can be selected from the group consisting of antibody, Fab', aptamer, antigen, hormone, growth factor, receptor, protein and nucleic acid. The kits can also include instruction for particle elemental analysis.

The kits can comprise the following components:
(a) In situ amplification reagents
(b) nucleic acid purification reagents and devices
(c) In situ hybridization buffer
(d) fixation and permeabilization solution
(e) washing solution
(f) dissolving reagent The applicant's teaching provides the methods disclosed above. The methods allow for:
(a) Multiplexing
(b) simultaneous analysis of protein and gene expression
(c) methods with or without amplification steps
(d) low cost analysis without costly polymerase enzymes
(e) gene analysis in a single cell
(f) absolute quantitation of gene expression U.S. patent application Ser. No. 11/674,513, filed Feb. 13, 2007, and U.S. Provisional Patent Application 60/772,588, filed Feb. 13, 2006 are incorporated herein by reference in their entirety. Additionally, all references cited in the disclosure are herein incorporated by reference in their entirety.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

REFERENCE LIST

1. Lockhart, D. J., Chee, M., Gunderson, K., Lai, C., Wodicka, L., Cronin, M. T., Lee, D., Tran, H. M., Matsuzaki, H., Gall, G. H., Barone, A. D., Mcgall, G. H., Chaoqiang, L., and Lee, D. H. Identifying differences in nucleic acid levels between samples—using arrays comprising probe oligo:nucleotide(s) which can form hybrid duplexes with nucleic acids in the samples. AFFYMETRIX INC, Lockhart, D. J., Chee, M., Gunderson, K., Lai, C., Wodicka, L., Cronin, M. T., Lee, D. H., Tran, H. M., Matsuzaki, H., Mcgall, G. H., and Barone, A. D. [EP880598-A; WO9727317-A; WO9727317-A1; AU9722533-A; EP880598-A1; U.S. Pat. No. 6,344,316-B1; JP2002515738-W; US2003064364-A1; U.S. Pat. No. 6,858,711-B2; US2005158772-A1; US2005191646-A1].
2. Pease, A. C.; Solas, D.; Sullivan, E. J.; Cronin, M. T.; Holmes, C. P.; Fodor, S. P. A. Light-Generated Oligonucleotide Arrays for Rapid Dna-Sequence Analysis *Proceedings of the National Academy of Sciences of the United States of America* 1994, 91, 502-26.
3. Guo, Z.; Guilfoyle, R. A.; Thiel, A. J.; Wang, R.; Smith, L. M. Direct fluorescence analysis of genetic polymorphisms by hybridization with oligonucleotide arrays on glass supports *Nucleic Acids Res.* 1994, 22, 5456-65.
4. Gravitt, P. E.; Peyton, C. L.; Apple, R. J.; Wheeler, C. M. Genotyping of 27 human papillomavirus types by using L1 consensus PCR products by a single-hybridization, reverse line blot detection method *Journal of Clinical Microbiology* 1998, 36, 3020-27.
5. Rosenberg, M., Debouck, C., and Bergsma, D. Methods and compsns. for identifying genes which are differentially expressed—in a normal healthy animal and an animal having a selected disease or infection. SMITHKLINE BEECHAM CORP. [WO9521944-A; EP743989-A; EP743989-A4; WO9521944-A1; EP743989-A1; JP9508800-W].
6. Lipshutz, R. J.; Fodor, S. P.; Gingeras, T. R.; Lockhart, D. J. High density synthetic oligonucleotide arrays *Nat. Genet.* 1999, 21, 20-24.
7. Churchill, G. A. Fundamentals of experimental design for cDNA microarrays *Nat. Genet.* 2002, 32 Suppl, 490-95.
8. Churchill, G. A. Fundamentals of experimental design for cDNA microarrays *Nat. Genet.* 2002, 32 Suppl, 490-95.
9. Weeraratna, A. T.; Nagel, J. E.; Mello-Coelho, V.; Taub, D. D. Gene expression profiling: from microarrays to medicine *J Clin. Immunol.* 2004, 24, 213-24.
10. Wang, D., Li, G., Ma, X., Liu, C., Zhou, Y., and Cheng, J. Detecting a target nucleic acid molecule, for use in clinical diagnosis, comprises incubating the cell lysate, without nucleic acid purification, with a nucleic acid probe, allowing hybridization. UNIV QINGHUA and CAPITAL BIOCHIP CO LTD. [WO2005017193-A1; AU2003257371-A1; CN1580283-A].
11. Venkatasubbarao, S. Microarrays—status and prospects *Trends Biotechnol.* 2004, 22, 630-37.
12. Mullis, K. B., Arnheim, N., Saiki, R. K., Erlich, H. A., Horn, G. T., Scharf, S. J., Banks, Mullis K., and Keichi, Saiki R. Process for amplifying detecting or cloning nucleic acid sequences—useful in disease diagnosis and in prepn. of transforming vectors. CETUS CORP, HOFFMANN LA ROCHE & CO AG, and HOFFMANN LA, R. 0. C. H. [EP200362-A2; EP200362-A3; JP92067957-B2; JP92067960-B2; EP200362-A1; EP200362-B; EP200362-A; AU8655322-A; AU8655323-A; JP61274697-A; JP62000281-A; DK8601448-A; DK8601449-A; U.S. Pat. No. 4,683, 195-A; U.S. Pat. No. 4,683,202-A; ES8706822-A; ES8706823-A; ZA8602334-A; ZA8602335-A; ES8800356-A; ES8800357-A; CA1237685-A; U.S. Pat. No. 4,800,159-A; U.S. Pat. No. 4,683,202-B; IL78281-A; CA1291429-C; IL78284-A; JP92067957-B; JP92067960-B; EP200362-B1; DE3687537-G; JP6007166-A; DK171160-B; DK171161-B; JP2546576-B2; IE83456-B; IE83464-B; U.S. Pat. No. 4,683,195-B; CA1340121-E].
13. Kadkol, S. S.; Gage, W. R.; Pasternack, G. R. In situ hybridization—Theory and practice *Molecular Diagnosis* 1999, 4, 169-83.
14. Jonker, A.; deBoer, P. A. J.; vandenHoff, M. J. B.; Lamers, W. H.; Moorman, A. F. M. Towards quantitative in situ hybridization *Journal of Histochemistry & Cytochemistry* 1997, 45, 413-23.
15. Raap, A. K. Advances in fluorescence in situ hybridization *MutatRes.* 1998, 400, 287-98.
16. Tanke, H. J.; Dirks, R. W.; Raap, T. FISH and immunocytochemistry: towards visualizing single target molecules in living cells *Curr. Opin. Biotechnol.* 2005, 16, 49-54.
17. Levsky, J. M.; Singer, R. H. Fluorescence in situ hybridization: past, present and future *J Cell Sci.* 2003, 116, 2833-38.
18. Levsky, J. M.; Shenoy, S. M.; Pezo, R. C.; Singer, R. H. Single-cell gene expression profiling *Science* 2002, 297, 836-40.
19. Janicki, S. M.; Tsukamoto, T.; Salghetti, S. E.; Tansey, W. P.; Sachidanandam, R.; Prasanth, K. V.; Ried, T.; Shav-Tal, Y.; Bertrand, E.; Singer, R. H.; Spector, D. L. From silencing to gene expression: Real-time analysis in single cells *Cell* 2004, 116, 683-98.
20. Weier, H. U.; Chu, L. W.; Murnane, J. P.; Weier, J. F. Applications and technical challenges of fluorescence in situ hybridization in stem cell research *Blood Cells Mol. Dis.* 2004, 32, 68-76.
21. Derradji, H.; Bekaert, S.; Van Oostveldt, P.; Baatout, S. Comparison of different protocols for telomere length estimation by combination of quantitative fluorescence in situ hybridization (Q-FISH) and flow cytometry in human cancer cell lines *Anticancer Res.* 2005, 25, 1039-50.

22. Baranov, V. I.; Quinn, Z.; Bandura, D. R.; Tanner, S. D. A sensitive and quantitative element-tagged immunoassay with ICPMS detection *Analytical Chemistry* 2002, 74, 1629-36.
23. Zhang, Q. Y.; Garner, K.; Viswanatha, D. S. Rapid detection of leukemia-associated translocation fusion genes using a novel combined RT-PCR and flow cytometric method *Leukemia* 2002, 16, 144-49.
24. Stein, C. A.; Subasinghe, C.; Shinozuka, K.; Cohen, J. S. Physicochemical Properties of Phosphorothioate Oligodeoxynucleotides *Nucleic Acids Research* 1988, 16, 3209-21.
25. Sambrook et al., in Molecular Cloning: A Laboratory Manual, Cold Spring Harbor Laboratory Press (1989).
26. Ausubel et al., in Current Protocols in Molecular Biology, Greene Publishing Associates and Wiley-Intersciences (1987).

What is claimed is:

1. A method of analysis using an inductively coupled plasma mass spectrometer system, the method comprising:
   introducing a cellular sample comprising one or more cells or cellular particles into the inductively coupled plasma mass spectrometer system, the cellular sample comprising: (a) a first oligonucleotide probe coupled with a first metal tag, the first oligonucleotide probe complementary to and hybridized with a first target mRNA molecule of the cellular sample; and (b) an affinity reagent coupled with a second metal tag having an elemental or isotopic composition different than the first metal tag, the affinity reagent bound to a cell surface protein or an intracellular protein;
   assessing a protein expression of the cellular sample and assessing a gene expression of the cellular sample by detecting, with the inductively coupled plasma mass spectrometer system, the first metal tag and the second metal tag based on the elemental or isotopic compositions of the first and second metal tags.

2. The method of claim 1, wherein the cellular sample is prepared by:
   rendering the first target mRNA molecule available for hybridization by at least one of fixing and permeabilizing the one or more cells or cellular particles;
   incubating the cellular sample with the affinity reagent under conditions to enable the affinity reagent to bind with the cell surface protein or the intracellular protein;
   separating bound affinity reagent from unbound affinity reagent;
   incubating the cellular sample in a hybridization solution with the first oligonucleotide probe under conditions to enable the first oligonucleotide probe to hybridize to the first target mRNA molecule; and
   separating unhybridized first oligonucleotide probe from first oligonucleotide probe hybridized to the first target mRNA molecule.

3. The method of claim 1, wherein the affinity reagent comprises an antibody.

4. The method of claim 1, wherein the first metal tag comprises a metal labeled bead.

5. The method of claim 1, wherein the first metal tag comprises a chemical moiety that includes a plurality of atoms.

6. The method of claim 1, wherein the first target mRNA molecule is associated with a disease-relevant gene.

7. The method of claim 1, wherein the cellular sample comprises a bacterial sample and wherein the method further comprises identifying a bacteria based on the detection of a first metal tag and a second metal tag from the bacterial sample.

8. The method of claim 1, wherein the cellular sample further comprises a second oligonucleotide probe coupled with a third metal tag having an elemental or isotopic composition different than the first metal tag, the second oligonucleotide probe hybridized with a second target nucleic acid of the cellular sample that is different than the first target mRNA; and wherein the method further comprises detecting the third metal tag based on the elemental or isotopic composition of the third metal tag.

9. A method of using an inductively coupled plasma mass spectrometer system for analysis of a cellular sample having one or more cells or cellular particles, the method comprising:
   rendering a target nucleic acid available for hybridization to complementary oligonucleotide probes by at least one of fixing and permeabilizing the one or more cells or cellular particles of the cellular sample, wherein the complementary oligonucleotide probes comprise a nucleic acid sequence that is complementary to the target nucleic acid;
   incubating the cellular sample in a hybridization solution comprising the complementary oligonucleotide probes under conditions to enable the complementary oligonucleotide probes to hybridize to the target nucleic acid through complementary base pairing between the complementary oligonucleotide probes and the target nucleic acid;
   separating unhybridized complementary oligonucleotide probes from complementary oligonucleotide probes hybridized to the target nucleic acid;
   labeling the complementary oligonucleotide probes with a unique metal tag such that the complementary oligonucleotide probes are distinguishable by the inductively coupled plasma mass spectrometer from any other oligonucleotide probe labeled with a metal tag having an elemental or isotopic composition different than the unique metal tag; and detecting the unique metal tag associated with the complementary oligonucleotide probes hybridized to the target nucleic acid with the inductively coupled plasma mass spectrometer system by detecting, with the inductively coupled plasma mass spectrometer system, the unique metal tag labeling the complementary oligonucleotide probes.

10. The method of claim 9, further comprising quantifying a gene expression level of the cellular sample based on the detection and measurement of the unique metal tag.

11. The method of claim 10, further comprising incubating the cellular sample with an affinity reagent under conditions to enable the affinity reagent to bind with a cell surface protein or an intracellular protein; separating bound affinity reagent from unbound affinity reagent; quantifying protein expression of the cellular sample by detecting and measuring a metal tag associated with the affinity reagent using the inductively coupled plasma mass spectrometer.

12. The method of claim 9, wherein the cellular sample comprises a single cell.

13. The method of claim 9, wherein incubating the cellular sample in the hybridization solution with the complementary oligonucleotide probes comprises incubating the cellular sample in the hybridization solution with a biotin labeled oligonucleotide probe; and wherein labeling the complementary oligonucleotide probes with the unique metal tag comprises reacting the biotin labeled complementary oligonucleotide probe with streptavidin labeled with the unique metal tag.

14. The method of claim 9, further comprising incubating the cellular sample with an affinity reagent under conditions to enable the affinity reagent to bind with a cell surface protein or an intracellular protein; separating bound affinity reagent from unbound affinity reagent; quantifying protein expression of the cellular sample by detecting and measuring a metal tag associated with the affinity reagent using the inductively coupled plasma mass spectrometer.

15. The method of claim 14, wherein the affinity reagent comprises an antibody.

16. The method of claim 9, wherein each unique metal tag comprises a chemical moiety that includes a plurality of atoms.

17. The method of claim 9, wherein the unique metal tag comprises a metal labeled bead.

18. A method of detecting a presence or absence of a target nucleic acid in a cellular sample, the method comprising:

introducing a cellular sample into an inductively coupled plasma mass spectrometer, the cellular sample prepared by (a) incubating the cellular sample in a hybridization solution comprising oligonucleotide probes that are complementary to the target nucleic acid, (b) separating unhybridized complementary oligonucleotide probes from any complementary oligonucleotide probes hybridized to the target nucleic acid, and (c) labeling the complementary oligonucleotide probes with a unique metal tag such that the complementary oligonucleotide probes are distinguishable by the inductively coupled plasma mass spectrometer;

detecting the presence or absence of the target nucleic acid in the cellular sample by detecting, with the inductively coupled plasma mass spectrometer, a presence or absence of the unique metal tag based on the elemental or isotopic composition of the unique element tag.

19. The method of claim 18, wherein the complementary oligonucleotide probes comprise carboxyl-modified oligonucleotides that attach the unique metal tag through functional chemistry.

20. The method of claim 18, wherein the complementary oligonucleotide probes comprise amino allyl-modified oligonucleotides that attach the unique metal tag through functional chemistry.

21. The method of claim 18, wherein the complementary oligonucleotide probes are biotinylated and wherein the unique metal tag comprises a metal labeled streptavidin.

22. A method of analysis using a means for elemental analysis, the method comprising:

introducing a cellular sample comprising one or more cells or cellular particles into the means for elemental analysis, the cellular sample comprising: (a) a probe hybridized with a first target mRNA molecule, the probe coupled with a first metal tag;

assessing a gene expression of the cellular sample by detecting, with the means for elemental analysis, the first metal tag based on the elemental or isotopic compositions of the first metal tag.

* * * * *